United States Patent
Xiong et al.

(10) Patent No.: US 9,968,633 B2
(45) Date of Patent: May 15, 2018

(54) STIMULI RESPONSIVE COMPOSITIONS FOR IRON CHELATION

(71) Applicants: May Pang Xiong, Middleton, WI (US); Zhi Liu, Madison, WI (US); Yan Wang, Madison, WI (US)

(72) Inventors: May Pang Xiong, Middleton, WI (US); Zhi Liu, Madison, WI (US); Yan Wang, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days. days.

(21) Appl. No.: 14/876,740

(22) Filed: Oct. 6, 2015

(65) Prior Publication Data

US 2016/0184344 A1    Jun. 30, 2016

Related U.S. Application Data

(60) Provisional application No. 62/061,008, filed on Oct. 7, 2014, provisional application No. 62/116,305, filed on Feb. 13, 2015.

(51) Int. Cl.
| | |
|---|---|
| *A61K 31/785* | (2006.01) |
| *C08F 220/28* | (2006.01) |
| *C08F 230/04* | (2006.01) |
| *A61K 47/48* | (2006.01) |
| *C08B 37/16* | (2006.01) |
| *C08L 5/16* | (2006.01) |

(52) U.S. Cl.
CPC ........ *A61K 31/785* (2013.01); *A61K 47/4823* (2013.01); *A61K 47/48176* (2013.01); *A61K 47/48784* (2013.01); *C08B 37/0012* (2013.01); *C08B 37/0015* (2013.01); *C08L 5/16* (2013.01); *C08F 2220/282* (2013.01)

(58) Field of Classification Search
CPC .......... A61K 47/48176; A61K 47/4823; A61K 47/48784; C08B 37/0015; C08F 2220/282; C08F 230/04
See application file for complete search history.

(56) References Cited

U.S. PATENT DOCUMENTS

2012/0021036 A1* 1/2012 Majeti .............. A61K 47/48238
                                                           424/422

OTHER PUBLICATIONS

Rossi et al. (Macromolecules, 2008, 41, 5272-5282).*
Nakahata et al. (Nature Communications: Redox-responsive self-healing materials formed from host-guest polymers, Oct. 25, 2011).*
Feng et al., Electrochemical redox responsive polymeric micelles formed from amphiphilic supramolecular brushes, Chem. Commun., 2014, 50, 4740(3 pages).
Feng et al., Self-Assembly of Amphiphilic Homopolymers Bearing Ferrocene and Carboxyl Functionalities: Effect of Polymer Concentration, B-Cyclodextrin, and Length of Alkyl Linker, Langmuir 2013, 29, pp. 10922-10931.
Imran ul-haq et al., Design of Long Circulating Nontoxic Dendritic Polymers for the Removal of Iron in Vivo, American Chemical Society, 2013, vol. 7, No. 12, pp. 10704-10716.
Ratcliffe, et al., From a Water-Immiscible Monomer to Block Copolymer Nano-Objects via a One-Pot RAFT Aqueous Dispersion Polymerization Formulation, Macromolecules, 2013, 46, pp. 769-777.

* cited by examiner

*Primary Examiner* — Anna Falkowitz
(74) *Attorney, Agent, or Firm* — Foley & Lardner LLP; Joseph P. Meara; Melissa El Menaouar

(57) ABSTRACT

The present technology provides new compositions comprising at least one cross-linked co-polymer. In some embodiments, the polyacrylamide co-polymer comprises water soluble subunits, cross-linking subunits, and iron chelating subunits. In other embodiments, the co-polymer comprises water soluble units, cross-linking subunits, and substituted subunits, which can be conjugated with iron-chelating agents. When these new particles are exposed to certain environments, such the presence of strong acids or oxidation agents, these particles are capable of breaking up so that the iron chelating agents can chelate iron or other metals from their environments. Methods to prepare these new compositions are also provided. These compositions or compositions comprising nanogels of the present technology may be used to treat metal overload conditions such as iron overload resulting from chronic transfusions.

19 Claims, 12 Drawing Sheets

FIG. 11A
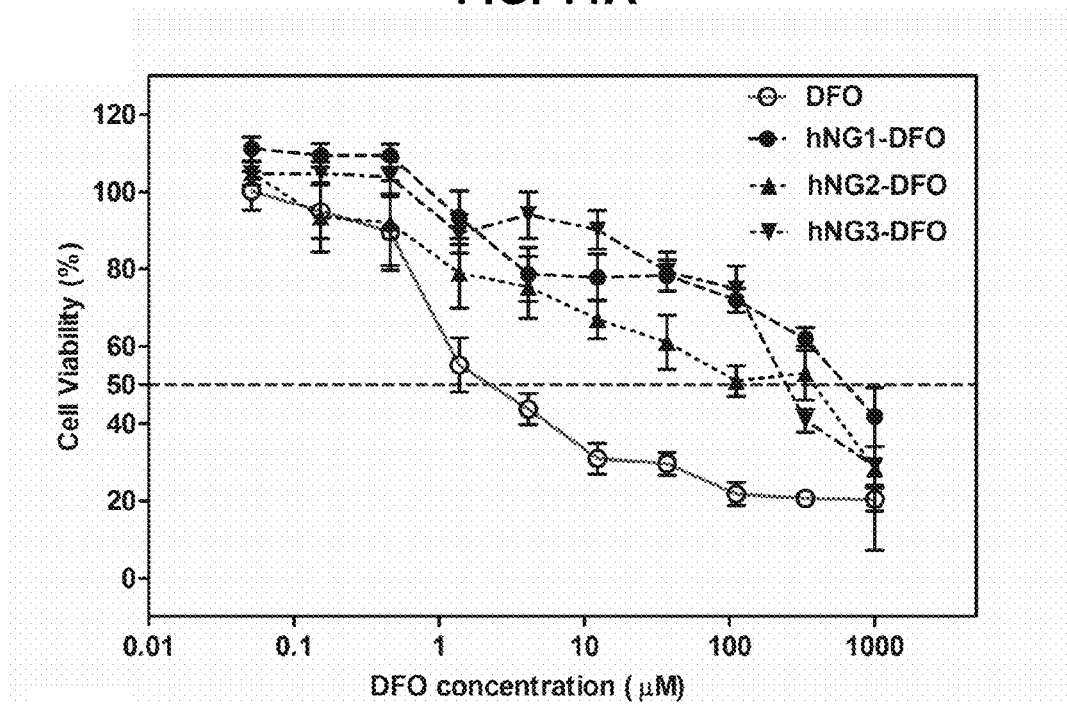
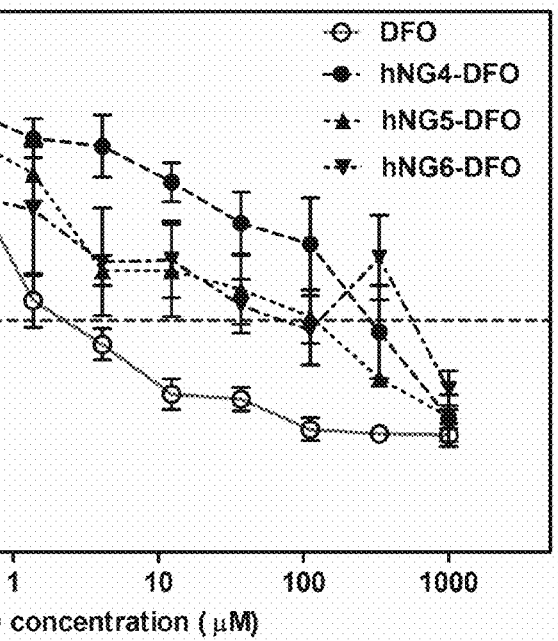
FIG. 11B

STIMULI RESPONSIVE COMPOSITIONS FOR IRON CHELATION

RELATED APPLICATIONS

This application claims priority to U.S. Provisional Application Ser. No. 62/061,008, filed Oct. 7, 2014, and to U.S. Provisional Application Ser. No. 62/116,305, filed Feb. 13, 2015, which are hereby incorporated by reference in their entireties.

STATEMENT OF GOVERNMENT SUPPORT

This invention was made with government support under R01DK099596 awarded by the National Institutes of Health. The government has certain rights in the invention.

FIELD OF THE TECHNOLOGY

The present technology relates to new stimuli responsive compositions comprising cross-linked copolymers. Specifically, new compositions comprising at least one cross-linked co-polymer that in turn comprises soluble subunits, cross-linking subunits, and iron chelating subunits are capable of chelating iron (II) and/or (III) ions.

BACKGROUND

Iron overload or hemochromatosis is a disease characterized by an accumulation of iron in the body. Symptoms manifest themselves due to genetic abnormalities (hereditary hemochromatosis, sickle cell anemia), through blood transfusions, or from disease treatments like chemotherapy which can induce anemia and require numerous blood transfusions. The overabundance of iron in the blood leads to tissue damage and organ failure if not properly treated.

Presently, the most common treatment for iron overload is deferoxamine (DFO), an iron chelator. This drug can chelate both the $Fe^{2+}$ and $Fe^{3+}$ forms of the iron ion. Unfortunately, the drug suffers from a poor half-life and dangerous side effects. Two more recently developed drugs for iron overload are deferasirox and deferiprone. Although both display longer half-lives and improved safety profiles compared to DFO, they still give rise to safety and patient compliance issues. In particular, each drug can only bind one of the two forms of ionized iron, and must typically be administered together. The CDC estimates that iron overloading is estimated to occur in up to 6 people per 100 in the US.

SUMMARY

The present technology provides compositions for use in chelating excess iron, particularly in vivo. The compositions include cross-linked polyacrylyl copolymers that form nano-sized structures, such as nanogels, and can chelate either or both iron(II) and iron(III) in the bloodstream. The nanostructures of the present composition are designed to drastically extend chelator pharmacokinetics in comparison to the short half-lives of small molecule chelators such as DFO. In addition, the nanostructures of the present compositions are subject to stimuli-controlled disassembly into components small enough for renal and biliary clearance. Such stimuli-responsive disassembly provides for efficient removal of iron-bound chelates, similar to the rapid elimination of small molecule chelators from the body.

In one aspect, the present technology provides new compositions that include at least one cross-linked polyacrylyl co-polymer that in turn includes water soluble acrylyl subunits, stimuli-responsive cross-linking subunits, and iron-chelating subunits. The compositions are in the form of a nano-sized structure such as a nano-particle that exists in water as a hydrogel (e.g., a nanogel). The water soluble subunits are derived from acrylamido and/or acrylic monomers. The stimuli-responsive cross-linking subunits are derived from hydrolyzable diacrylyl monomers or redox-sensitive diacrylyl complexes, and the iron-chelating subunits are derived from polymerizable monomers, such as an acrylyl or vinyl monomers, comprising an iron chelating group. The new compositions are sensitive to the hydrolytic or oxidative state of their environments. In response to changes in these environments, the nanostructures can break up and release smaller polymers that include iron chelates and are rapidly cleared from the body.

The present technology also provide methods of preparing the new compositions of cross-linked polyacrylyl co-polymers. The methods include polymerizing a mixture water soluble monomers, stimuli-responsive cross-linking monomers or monomer complexes, and iron chelating monomers or substituted monomers. Each of these monomers (as defined herein) provides the corresponding subunit derived from the monomers, i.e., water soluble subunits, stimuli-responsive cross-linking subunits, and iron chelating subunits or substituted subunits as defined herein. Where the cross-linked acrylyl copolymer includes subunits derived from substituted monomers, the methods further include conjugating an iron-chelating agent to the substituted subunits of the composition.

In another aspect, the present technology provides methods of treating subjects at risk for or suffering from excess iron ("iron overload") or other excess metals similar to iron. In the methods, the present compositions are administered to a subject at risk for or suffering from excess iron (or similar metal) an effective amount of a composition as described herein. Upon degradation of the composition due to hydrolysis or due to direct oxidation of, e.g., a ferrocenyl iron (which has, e.g., a reversible redox potential of ±0.4 V with respect to Ag/AgCl), the constituent polymers are expected to clear from the body by the renal and/or hepatic route.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIGS. 11A and 11B show cytotoxicity profiles for HUVEC cells incubated with free DFO and hNG-DFOs.

DETAILED DESCRIPTION

Figure 1:
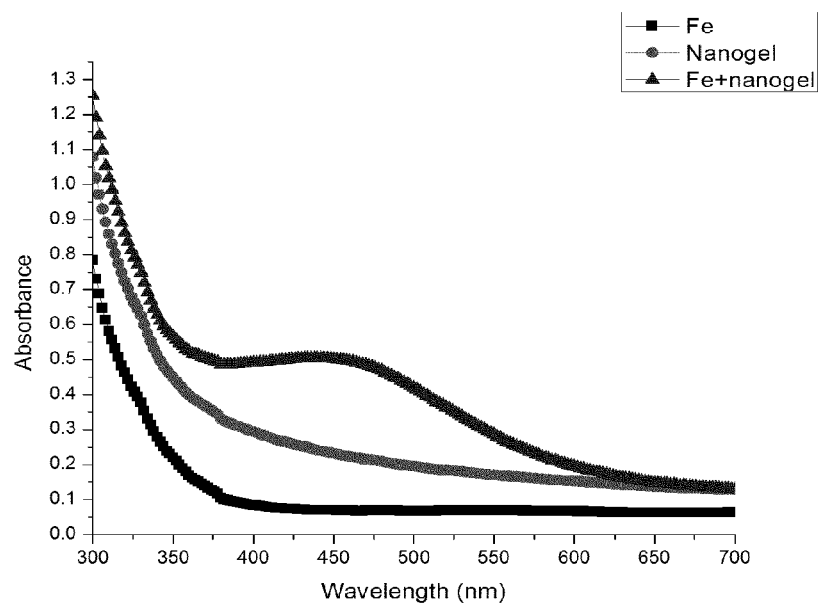
FIG. 1 shows Example 1 results: Fe(III) solution at 0.01 mg/mL does not absorb at 430 nm (square); NG-DFO solution at 0.5 mg/mL reveals minimal absorbance at 430 nm (circle); after mixing Fe(III) and NG-DFO, a distinct clear yellow-brown color immediately forms (triangle), indicative of NG-DFO:Fe(III) chelates. The absorbance peak at 430 nm verifies this result and again confirms successful incorporation of DFOm into the backbone of nanogels during reverse emulsion polymerization.

In one aspect, the present technology provides new compositions that include at least one cross-linked polyacrylyl co-polymer that comprises water soluble acrylyl subunits, stimuli-responsive cross-linking subunits, and iron-chelating subunits. The compositions are typically nanogels. The water soluble subunits are derived from acrylamido and/or acrylic monomers. The stimuli-responsive cross-linking subunits are derived from hydrolyzable diacrylyl monomers or redox-sensitive diacrylyl complexes; and the iron-chelating subunits are derived from polymerizable monomers, such as acrylyl or vinyl monomers, comprising an iron chelating group.

As used herein, a subunit in the acrylyl co-polymer is considered to be "derived from" a monomer when the subunit results from polymerization of the corresponding monomer. For example, a subunit is derived from acrylic acid, when the latter forms part of a polymer and is attached to at least one and generally two other subunits. In another example, as shown below, an acrylamide monomer is converted into an acrylamido subunit by polymerization so that it is attached to two other subunits at the former vinyl carbons.

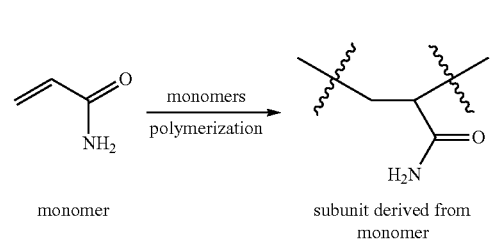

monomer        subunit derived from monomer

As use herein, the term "acrylyl" refers to any monomer or polymer that includes the C=C—C=O structure. Thus, in some embodiments, the water soluble acrylyl subunits are derived from one or more monomers selected from the group consisting of acrylamide, alkacrylamide, acrylic acid, alkacrylic acid, hydroxylalkyl acrylate, hydroxylalkyl alkacrylate, aminoalkyl acrylate, aminoalkyl alkacrylate, pegylated acrylamide, pegylated alkacrylamide, pegylated acrylate, and pegylated alkacrylate. Alkacrylamide, alkacrylic acid and alkacrylate respectively refer to acrylamide, acrylic acid and an ester of acrylic acid in which the vinyl group bears a substituted or unsubstituted C$_{1-4}$ alkyl group at one of the carbons. In some embodiments of alkacrylamides, alkacrylic acids and alkacrylates, the vinyl group bears a methyl group, e.g., methacrylic acid, methacrylate and methacrylamide. Pegylated monomers include a polyethylene glycol moiety (PEG) attached through an ester or amide linkage at the carboxyl of acrylic acid or alkacrylic acids. The PEG may include from 1 to 200 repeating ethyleneoxy groups, including 1, 2, 3, 4, 5, 10, 20, 30, 40, 50, 100, 150, or 200 such groups and any range between and including any of the foregoing values. The PEG may be capped with a substituted or unsubstituted C$_{1-4}$ alkyl group.

In certain embodiments, the water soluble acrylyl subunits are derived from one or more monomers selected from the group consisting of acrylamide, methacrylamide, acrylic acid, methacrylic acid, 2-hydroxyethyl methacrylate, N,N-diethylaminoethyl methacrylate, pegylated acrylamide, pegylated methacrylamide, pegylated acrylate, and pegylated methacrylate.

In some embodiments, the cross-linked polyacrylyl co-polymer comprises water soluble acrylyl subunits derived from acrylamide and/or acrylic acid monomers. In some such embodiments, the cross-linked polyacrylyl co-polymer further comprises one or more subunits derived from monomers selected from the group consisting of 2-hydroxyethyl methacrylate, N,N-diethylaminoethyl methacrylate, pegylated acrylamide, pegylated methacrylamide, pegylated acrylate, and pegylated methacrylate.

The iron-chelating subunits may be derived from polymerizable monomers containing an iron chelating group. Iron chelating groups that may be used include but are not limited to bidentate, tridentate, tetradentate, pentadentate and hexadentate ligands capable of coordinating to iron. Hexadentate ligands can coordinate to iron at up to six sites in an octahedral fashion. The iron chelating group may bind to $Fe^{2+}$ ions or $Fe^{3+}$ ions. In some embodiments the iron-chelating group binds to both $Fe^{2+}$ ions and $Fe^{3+}$ ions. In certain embodiments, the iron chelating group binds to $Fe^{3+}$ with a binding constant of at least 19 ($pFe^{3+}$), or at least 20, at least 21, at least 22, at least 23, at least 24, at least 25, at least 26, at least 27, at least 28, at least 29, at least 30, at least 31, at least, 32, at least 33, at least 34, at least 35, at least 36, or a range between and including any two of the foregoing values, e.g., 19-36 or 19-26 ($pFe^{3+}$).

In some embodiments, the iron-chelating subunits are represented by Formula I or II,

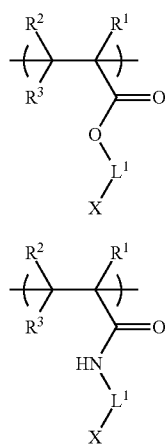

wherein $R^1$ at each occurrence is independently H, CN, or a $C_{1-4}$ alkyl group; $R^2$ and $R^3$ at each occurrence are independently H or methyl; $L^1$ at each occurrence is independently a substituted or unsubstituted $C_{1-12}$ alkylene, substituted or unsubstituted $C_{1-12}$ heteroalkylene, or —$(CH_2CH_2O)_n$—, wherein n is 1, 2, 3, or 4; and X at each occurrence is independently an iron chelating group.

In certain embodiments, the iron-chelating monomers have a structure selected from one or more of Formula IV-A, IV-B, IV-C, or IV-D,

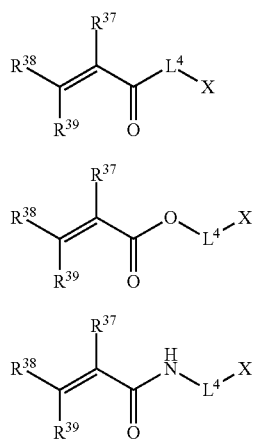

wherein $R^{38}$ and $R^{39}$ are independently H or methyl; $R^{37}$ is H, CN, or a $C_{1-4}$ alkyl group; $L^4$ is a substituted or unsubstituted $C_{1-12}$ alkylene, substituted or unsubstituted $C_{1-12}$ heteroalkylene, or —$(CH_2CH_2O)_n$—, wherein n is 1, 2, 3, or 4; and X is at each occurrence is independently an iron chelating group.

In certain embodiments of the iron-chelating subunits represented by Formulae I, II, IV-A, IV-B, IV-C and IV-D, X is a group comprising one or more of a hydroxamic acid, pyridine, thiazolidine, hydroxyl, phenol or carboxylic acid (e.g., acetic acid) groups. By way of non-limiting example, X may be selected from deferoxamine, deferiprone, ethylenediaminetetraacetic acid, epyridoxal isonicotinoyl hydrazone, rhodotorulic acid, N,N'-Bis(2-hydroxybenzyl)ethylenediamine-N,N'-diacetic acid, N,N'-Bis(2-hydroxybenzyl) propylene-1,3-diamine-N,N'-diacetic acid, pyridoxal isonicotinoyl hydrazone, or 2,3-dihydroxybenzoic acid.

In some embodiments where the iron chelating subunits are represented by any of the Formulae herein (e.g., Formulae I, II, IV-A, IV-B, IV-C and IV-D), $R^1$ (or $R^{37}$) is a methyl, $R^2$ and $R^3$ (or $R^{38}$ and $R^{39}$) are H, $L^1$ (or $L^4$) is ethylene, and X is deferoxamine.

The stimuli-responsive cross-linking subunits respond to certain types of changes in the environment of the acrylyl copolymer such as changes in the hydrolytic environment or the oxidation/reduction potential of the environment. The corresponding monomer(s) or monomer complexes from which each subunit is derived contains two polymerizable groups and can be linked to other subunits at two different points. The cross-linking monomers or monomer complexes may therefore attach to and cross-link the same co-polymer or two different co-polymers. For example, stimuli-responsive cross-linking subunits responsive to hydrolytic conditions may be derived from hydrolyzable diacrylate ester monomers. Redox-sensitive subunits are derived from monomer complexes containing typically two monomers, which form a single diacrylyl group under reducing conditions and disassociate under oxidizing conditions. For example, stimuli-sensitive cross-linking subunits may be derived from the cross-linking subunits are derived from hydrolyzable diacrylate monomers, redox-sensitive diacrylamide monomer complexes, hydrolyzable acrylate-acrylamide monomers, hydrolyzable vinyl-acrylate monomers, redox-sensitive vinyl-acrylamide monomer complexes, and redox-sensitive divinyl monomer complexes.

In some embodiments, the cross-linking subunits are derived from poly(ethylene glycol) diacrylates monomers of Formula III-A,

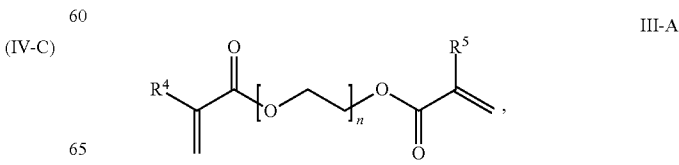

wherein $R^4$ and $R^5$ are independently H, CN, or a $C_{1-4}$ alkyl group; and n is 1 to 20.

In certain embodiments, the cross-linked polyacrylyl copolymer further comprises one or more subunits derived from monomers of Formula III-B or III-C,

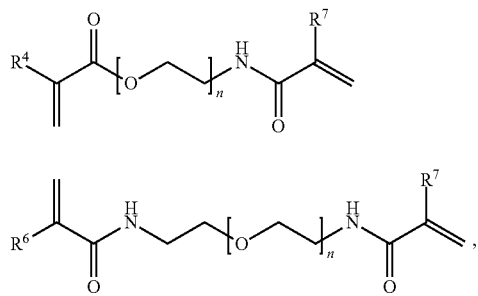

III-B

III-C wherein $R^6$ and $R^7$ are independently H, CN, or a $C_{1-4}$ alkyl group; and n is 1 to 20.

As noted above, the cross-linking subunits in Formula III-A and III-B may have from 1 to 20 repeating units. In some embodiments, the cross-linking subunits in Formula III-A, and III-B may have 1, 2, 3, 4, 5, 6, 7, 8, 9, 10, 11, 12, 13, 14, 15, 16, 17, 18, 19, or 20 repeating units or a range between and including any two of the foregoing values.

The stimuli-responsive cross-linking subunits may be derived from other diacrylyl monomers. Diacrylyl monomers suitable for use herein may have the structures of the Formula VI-A or VI-B:

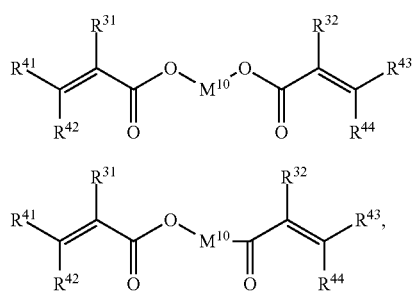

(VI-A)

(VI-B)

wherein $R^{31}$ and $R^{32}$ are independently H, CN, or a $C_{1-4}$ alkyl group, $R^{41}$, $R^{42}$, $R^{43}$, and $R^{44}$ are independently H or methyl; $M^{10}$ is selected from a substituted or unsubstituted $C_{1-12}$ alkylene; substituted or unsubstituted $C_{1-12}$ heteroalkylene; or —$(CH_2CH_2O)_n$—, wherein n is 1, 2, 3, or 4.

Similarly, the diacrylyl monomers suitable for use in the present technology may have the structures of the Formula VI-C or VI-D:

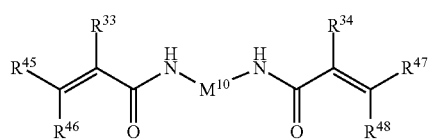

(VI-C)

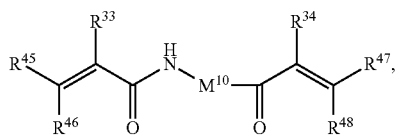

(VI-D)

wherein $R^{33}$ and $R^{34}$ are independently H, CN, or a $C_{1-4}$ alkyl group, $R^{45}$, $R^{46}$, $R^{47}$, and $R^{48}$ are independently H or methyl; $M^{11}$ is selected from a substituted or unsubstituted $C_{1-12}$ alkylene; substituted or unsubstituted $C_{1-12}$ heteroalkylene; or —$(CH_2CH_2O)_n$—, wherein n is 1, 2, 3, or 4.

In some embodiments, the cross-linking subunits are redox sensitive cross-linking subunits and may be derived from redox sensitive diacrylyl monomer complexes. Such redox sensitive cross-linking subunits respond to oxidizing environments/agents by disassociating. For example, the redox sensitive cross-linking subunits may comprise ferrocenyl-containing subunits and ferrocenyl-binding subunits.

In some embodiments, the ferrocenyl-binding subunits have a structure selected from one or more of Formula V-A, V-B, VI-A, or VI-B:

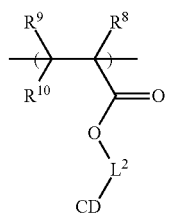

(V-A)

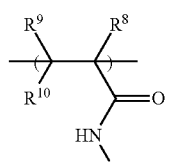

(V-B)

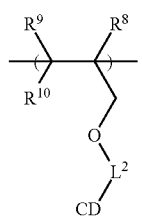

(V-C)

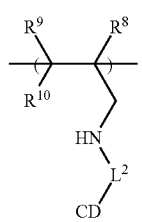

(V-D)

Wherein CD at each occurrence is independently a ferrocenyl-binding cyclodextrin; $R^8$ at each occurrence is independently H, CN, or a $C_{1-4}$ alkyl group; $R^9$ and $R^{10}$ at each occurrence are independently H or methyl; and $L^2$ at each occurrence independently selected from a substituted or unsubstituted $C_{1-12}$ alkylene, substituted or unsubstituted $C_{1-12}$ heteroalkylene, or —$(CH_2CH_2O)_n$—, wherein n is 1, 2, 3, or 4.

In some other embodiments, the ferrocenyl-containing subunits have a structure selected from one or more of Formula VII-A, VII-B, VII-C, VII-D, VII-E, VII-F, or VII-G:

(VII-A)
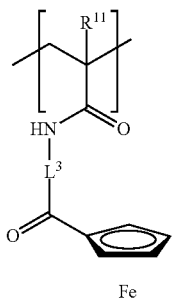

(VII-B)
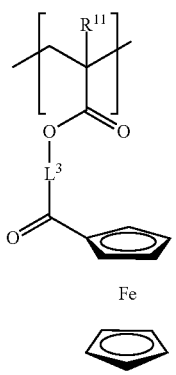

(VII-C)
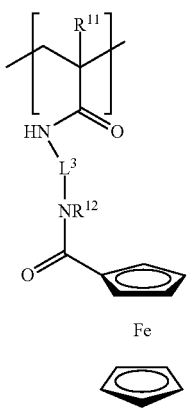

(VII-D)
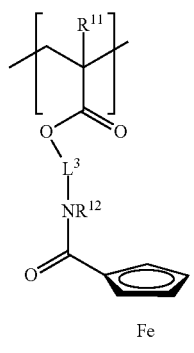

(VII-E)
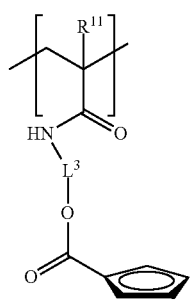

(VII-F)
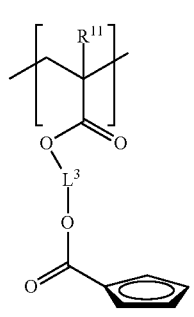

(VII-G)
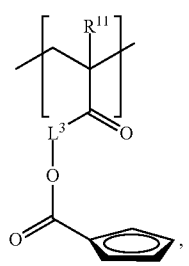

Wherein $R^{11}$ and $R^{12}$ at each occurrence are independently selected from H, CN, or a $C_{1-4}$ alkyl group; and $L^3$ at each occurrence is a substituted or unsubstituted $C_{1-6}$ alkylene, or $C_{1-6}$ heteroalkylene group.

In some embodiments, wherein the redox-sensitive cross-linking subunits are derived from redox-sensitive monomer complexes having the following structure,

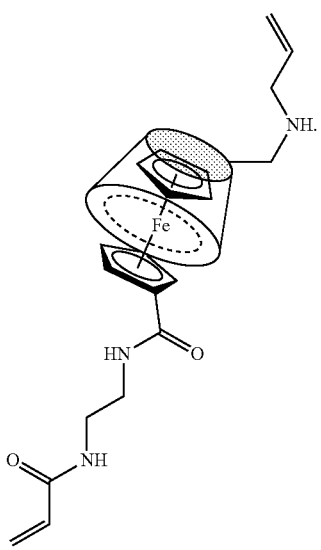

In yet another aspect, the present technology provides new compositions comprising at least one cross-linked co-polymer that comprises water soluble subunits, stimuli-response cross-linking subunits, and substituted subunits; wherein the water soluble subunits are derived from one or more monomers selected from group consisting of acrylamide, alkacrylamide, acrylic acid, alkacrylic acid, hydroxylalkyl acrylate, hydroxylalkyl alkacrylate, aminoalkyl acrylate, aminoalkyl alkacrylate, pegylated acrylamide, pegylated alkacrylamide, pegylated acrylate, and pegylated alkacrylate; the stimuli-responsive cross-linking subunits are derived from hydrolyzable diacrylate monomers, redox-sensitive diacrylamide monomer complexes, hydrolyzable acrylate-acrylamide monomers, hydrolyzable vinyl-acrylate monomers, redox-sensitive vinyl-acrylamide monomer complexes, and redox-sensitive divinyl monomer complexes; and the substituted subunits are derived from monomers represented by Formula XIII or XIV,

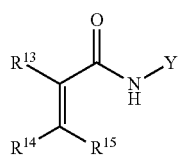
(XIII)

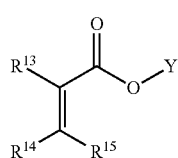
(XIV)

wherein $R^{13}$ at each occurrence is independently H, CN, or a $C_{1-4}$ alkyl group; $R^{14}$ and $R^{15}$ at each occurrence are independently H or methyl; Y is a substituted or unsubstituted $C_{1-12}$ alkylene, substituted or unsubstituted $C_{1-12}$ heteroalkylene, or $—(CH_2CH_2O)_n—$, wherein n is 1, 2, 3, or 4.

In some embodiments, the monomer of Formula XIV has the following structure:

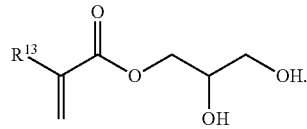

The composition in the present disclosure comprises a nanogel that has a size of from 10 to 500 nm. In some embodiments, the nanogel may have a size of from about 10 nm to 500 nm, from about 50 nm to about 450 nm, from about 50 nm to 250 nm, from about 100 nm to about 400 nm, from about 100 nm to 250 nm, from 150 nm to about 350 nm, from 200 nm to about 300 nm, from 250 nm to 275, or a range between and including any two of the foregoing values. As used herein, the term "about" refers to a range within 10% of the cited value.

The compositions of the present technology may have a wide variety of molecular weights. For example the present cross-linked copolymer may have a weight average molecular weight ranging from about 1,000 to about 10,000,000 kD. Exemplary molecular weights include 1,000, 2,000, 5,000, 10,000, 20,000, 50,000, 100,000, 200,000, 500,000, 1,000,000, 2,000,000, 5,000,000 and 10,000,000 kD or a range between and including any of the foregoing values, e.g., 10,000 to 1,000,000 or 10,000 to 100,000 kD.

In another aspect, the present nanogels or compositions including such nanogels may be used for the treatment of excess iron conditions (or other excess metals). Such overload typically occurs in subjects receiving chronic infusions of red blood cells for treatment of other conditions, diseases or disorders such as β-thalassemia, sickle cell anemia, Diamond black anemia and myelodysplastic syndromes. Hence, in one embodiment, the methods of treatment for excess iron include administering to a subject at risk for or suffering from excess iron an effective amount of one or more of the nanogels described herein. The subject is typically a mammal, e.g., a human, primate (e.g. monkey, chimpanzee, ape), cat, dog, pig, mouse, rat, horse, sheep, among others. In some embodiments, the subject is a human. In some embodiments, the subject suffers from excess iron due to a transfusion of red blood cells.

In another aspect the present technology provides compositions including pharmaceutical compositions. The compositions may include a pharmaceutically acceptable carrier, e.g., water, and any of the nanogels described herein, including salts thereof. In some embodiments, the present compositions include nanogels formed from the cross-linked copolymers. The compositions may be formulated for oral, rectal or parenteral administration, including intravenous, intramuscular, subcutaneous and nasal administration.

The instant technology also provides for compositions and medicaments including nanogels disclosed herein and a pharmaceutically acceptable carrier. Such compositions may be prepared by mixing nanogels of the present technology, pharmaceutically acceptable salts thereof, with pharmaceutically acceptable carriers, excipients, binders, diluents or the like to treat iron overload. The nanogels and compositions of the present technology may be used to prepare formulations and medicaments that treat iron overload caused by chronic blood infusions as used in the treatment of a variety of conditions, diseases or disorders. Such compositions can be in the form of, for example, granules, powders, tablets, capsules, creams, ointments, syrup, suppositories, injections, emulsions, elixirs, suspensions or solutions. The instant compositions can be formulated for various routes of administration, for example, by oral, parenteral, injection, rectal, nasal, or via implanted reservoir. Parenteral or systemic administration includes, but is not limited to, subcutaneous, intravenous, intraperitoneally, intramuscular, intrathecal, intracranial, and intracerebroventricular injections. The following dosage forms are given by way of example and should not be construed as limiting the instant technology.

For oral, buccal, and sublingual administration, powders, suspensions, granules, tablets, pills, capsules, gelcaps, and caplets are acceptable as solid dosage forms. These can be prepared, for example, by mixing nanogels disclosed herein, or pharmaceutically acceptable salts or stereoisomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions, which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Dosage units for rectal administration may be prepared in the form of suppositories which may contain the composition of matter in a mixture with a neutral fat base, or they may be prepared in the form of gelatin-rectal capsules which contain the active substance in a mixture with a vegetable oil or paraffin oil.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaqueous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver compounds of the present technology.

Aerosols containing compositions for use according to the present technology are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Delivery of aerosols of the present technology using sonic nebulizers is advantageous because nebulizers minimize exposure of the agent to shear, which can result in degradation of the compound.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the compounds may be formulated in oily solutions or as a gel. For administration of nasal aerosol, any suitable propellant may be used including compressed air, nitrogen, carbon dioxide, or a hydrocarbon based low boiling solvent.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant technology.

A therapeutically effective amount of a composition of the present technology may vary depending upon the route of administration and dosage form. Effective amounts of such compounds typically fall in the range of about 0.01 up to about 100 mg/kg/day, or about 0.05 to about 50 mg/kg/day, and more typically in the range of about 0.1 up to 5 mg/kg/day. Typically, the compound(s) (i.e., nanogel) of the instant technology are selected to provide a formulation that exhibits a high therapeutic index. The therapeutic index is the dose ratio between toxic and therapeutic effects and can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The nanogels of the present technology may be prepared using the reverse-emulsion technique. Briefly, an aqueous solution of the water soluble monomers is added to an immiscible liquid containing most or all of the other monomers, surfactant and initiator. The mixture is stirred and optionally heated until reaction is complete. Although the compositions and properties of the emulsion system affect the sizes of the nanogels in the present technology, it is well within the skill in the art to select different compounds, constituting monomers in various molar ratios, and initiators for the stepwise preparation of such nanogels.

In one aspect, the compositions of the present technology are formed by a process that comprises polymerizing a mixture of water soluble monomers, stimuli-responsive cross-linking monomers, and iron-chelating monomers or substituted monomers. The process is a reverse emulsion polymerization wherein the monomers are in aqueous solution/suspension and the solvent is an organic solvent (e.g., hexane, toluene, etc.). Typically, a standard initiator is used.

In another aspect, the compositions of the present technology are formed by a process that comprises polymerizing a mixture of water soluble monomers, stimuli-responsive cross-linking monomers, and substituted monomers. In some embodiments, the process to form the compositions of the present technology further comprises conjugating an iron-chelating agent to the substituted subunits of the compositions. A reverse emulsion may be used for these processes as well.

The following terms are used throughout this disclosure as defined below.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkoxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted cycloalkyl, aryl, aralkyl, heterocyclyl, heterocyclylalkyl, heteroaryl, and other cyclic groups also include rings and ring systems in which a bond to a hydrogen atom is replaced with a bond to a carbon atom. Therefore, substituted cycloalkyl, aryl, aralkyl, heterocyclyl, heterocyclylalkyl, heteroaryl, and other cyclic groups may also be substituted with substituted or unsubstituted alkyl, alkenyl, and alkynyl groups as defined below.

Alkyl groups include straight chain and branched chain alkyl groups having from 1 to 12 carbon atoms, or in some embodiments, from 1 to 8, 1 to 6, or 1, 2, 3, 4 or even 6 to 8 or 6 to 12 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, butadienyl, pentadienyl, and hexadienyl.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heteroalkyl groups are alkyl groups as defined herein in which one or more (but not all) carbon atoms have been replaced by a heteroatom such as O, N, or S. In some embodiments, the heteroalkyl group has 1 or 2 oxygen atoms or one or two nitrogen atoms, or 1 oxygen and 1 nitrogen atom. Thus alkoxy, alkylamino and alkoxyalkylamino are all examples of heteroalkyl groups.

Heterocyclyl groups are non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass partially unsaturated and saturated ring systems, such as, for example, imidazolinyl and imidazolidinyl groups, but not aromatic groups such as imidazolyl groups. The phrase "heterocyclyl group" includes fused ring species as well as bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, epoxy, thiaranyl, azetidinyl, oxetanyl, pyrrolidinyl, imidazolidinyl, pyrazolidinyl, thiazolidinyl, tetrahydrothiophenyl, tetrahydrofuranyl, dioxolyl, pyrrolinyl, imidazolinyl, pyrazolinyl, thiazolinyl, piperidinyl, piperazinyl, morpholinyl, thiomorpholinyl, tetrahydropyranyl, tetrahydrothiopyranyl, oxathiane, dithianyl, pyranyl, dihydropyridinyl, dihydrodithiinyl, dihydrodithionyl, homopiperazinyl, quinuclidyl, indolinyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, morpholinyl groups, which are 2-, 3-, 4-, 5-, or 6-substituted, or disubstituted with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol- 2-yl-propyl. Representative substituted heterocyclylalkyl groups may be substituted one or more times with substituents such as those listed above.

Groups described herein having two or more points of attachment (i.e., divalent, trivalent, or polyvalent) within the compound of the invention are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the invention are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms.

The term "carboxylate" as used herein refers to a —COOH group.

The term "ester" as used herein refers to —COOR$^{30}$ groups. R$^{30}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{31}$R$^{32}$, and —NR$^{31}$C(O)R$^{32}$ groups, respectively. R$^{31}$ and R$^{32}$ are independently hydrogen, or a substituted or unsubstituted alkyl, alkenyl, alkynyl, cycloalkyl, aryl, aralkyl, heterocyclylalkyl, or heterocyclyl group as defined herein. Amido groups therefore include but are not limited to carbamoyl groups (—C(O)NH$_2$) and formamide groups (—NHC(O)H). In some embodiments, the amide is —NR$^{31}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{33}$C(O)OR$^{34}$ and —OC(O)NR$^{33}$R$^{34}$ groups, respectively. R$^{33}$ and R$^{34}$ are independently a substituted or unsubstituted alkyl, alkenyl, alkynyl, cycloalkyl, aryl, aralkyl, heterocyclylalkyl, or heterocyclyl group as defined herein. R$^{33}$ may also be H.

The term "amine" (or "amino") as used herein refers to —NR$^{35}$R$^{36}$ groups, wherein R$^{35}$ and R$^{36}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{38}$R$^{39}$ and —NR$^{38}$SO$_2$R$^{39}$ groups, respectively. R$^{38}$ and R$^{39}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{40}$ groups, sulfoxides include —S(O)R$^{41}$ groups, sulfones include —SO$_2$R$^{42}$ groups, and sulfonyls include —SO$_2$OR$^{43}$. R$^{40}$, R$^{41}$, R$^{42}$, and R$^{43}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to NR$^{44}$—C(O)—NR$^{45}$R$^{46}$ groups. R$^{44}$, R$^{45}$, and R$^{46}$ groups are independently hydrogen, or a substituted or unsubstituted alkyl, alkenyl, alkynyl, cycloalkyl, aryl, aralkyl, heterocyclyl or heterocyclylalkyl group as defined herein.

The term "amidine" refers to —C(NR$^{47}$)NR$^{48}$R$^{49}$ and —NR$^{47}$C(NR$^{48}$)R$^{49}$, wherein R$^{47}$, R$^{48}$, and R$^{49}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{50}$C(NR$^{51}$)NR$^{52}$R$^{53}$, wherein R$^{50}$, R$^{51}$, R$^{52}$ and R$^{53}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{54}$)=C(R$^{55}$)NR$^{56}$R$^{57}$ and —NR$^{54}$C(R$^{55}$)=C(R$^{56}$)R$^{57}$), wherein R$^{54}$, R$^{55}$, R$^{56}$ and R$^{57}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxy" as used herein can refer to —OH or its ionized form, —O$^-$.

The term "imide" refers to —C(O)NR$^{58}$C(O)R$^{59}$, wherein R$^{58}$ and R$^{59}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{60}$(NR$^{61}$) and —N(CR$^{60}$R$^{61}$) groups, wherein R$^{60}$ and R$^{61}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{60}$ and R$^{61}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

Pharmaceutically acceptable salts of compounds described herein are within the scope of the present invention and include acid or base addition salts which retain the desired pharmacological activity and is not biologically undesirable (e.g., the salt is not unduly toxic, allergenic, or irritating, and is bioavailable). When the compound of the invention has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the invention has an acidic group, such as for example, a carboxylic acid or hydroxamic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that the nanogels of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the copolymers having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, imidazoles may exhibit the following isomeric forms, which are referred to as tautomers of each other:

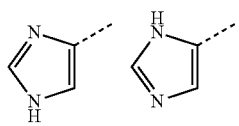

As readily understood by one skilled in the art, a wide variety of functional groups and other structures may exhibit tautomerism, and all tautomers of compounds as described herein are within the scope of the present invention.

Stereoisomers of compounds (also known as optical isomers) include all chiral, diastereomeric, and racemic forms of a structure, unless the specific stereochemistry is expressly indicated. Thus, compounds disclosed herein include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

"Treating" within the context of the instant technology, means an alleviation, in whole or in part, of symptoms associated with a condition, disorder or disease, or slowing, inhibition or halting of further progression or worsening of those symptoms in a subject suffering from the condition, disorder or disease, or prevention or prophylaxis of the disease or disorder in a subject at risk for developing the disease or disorder. For example, within the context of treating iron overload such as that caused by blood transfusions for the treatment of β-thalassemia, sickle cell anemia, and myelodysplastic syndromes, successful treatment may include clinical benefit, such as a reduction or elimination of toxic levels of free iron circulating in the blood stream, or an alleviation of symptoms. Symptoms of iron overload often vary between patients and may include fatigue, feelings of weakness, weight loss, abdominal pain, joint pain, abnormal puberty in adolescents and cessation of menstruation in women. In severe cases of iron overload, patients may present with gray or bronze-colored skin, shortness of breath, exercise intolerance, arthritis, liver disease, diabetes, and/or heart problems.

As used herein, a "therapeutically effective amount" of a compound or composition of the present technology refers to an amount of the compound or composition that alleviates, in whole or in part, symptoms associated with a condition, disorder or disease, or slows or halts of further progression or worsening of those symptoms, in a subject suffering from the condition, disease or disorder, or prevents or provides prophylaxis for the condition, disease or disorder in a subject at risk for developing the condition, disease or disorder.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology is further illustrated by the following examples, which should not be construed as limiting in any way.

EXAMPLES

Materials

Dioctyl sulfosuccinate (AOT), Brij 30, acrylamide (AAm), glycidyl methacrylate (GMA), sodium periodate ($NaIO_4$), sodium cyanoborohydride ($NaBH_3CN$), ferric chloride hexahydrate ($FeCl_3.6H_2O$) were purchased from Sigma-Aldrich (St. Louis, Mo.). Ferric ammonium citrate (FAC), ferrocenecarboxylic acid (Fc-COOH), N-Hydroxysuccinimide (NHS), β-cyclodextrin (β-CD), 1-(3-Dimethylaminopropyl)-3-ethylcarbodiimide hydrochloride (EDC), ethylenediamine (EDA), triethylamine (TEA), sodium hydroxide, p-toluenesulfonyl chloride (TsCl), allylamine and 1,4-dihydroxybenzene were purchased from VWR (Radnor, Pa.). β-CD was purified by recrystallization from water before use. Deferoxamine mesylate was obtained from the University of Wisconsin Hospital Pharmacy Services (Hospira). 2,2'-azobis[2-(2-imidazolin-2-yl)-propane]dihydrochloride (VA-044) was purchased from Wako Pure Chemical Industries, Ltd. Dulbecco's modified eagle medium (DMEM), heat-inactivated fetal bovine serum (FBS), penicillin/streptomycin solution (100×) and the Pierce BCA protein assay kit were purchased from Thermo Fisher Scientific (Waltham, Mass.). Mouse ferritin ELISA kit was purchased from Immunology Consultants Laboratory (Portland, Oreg.). All other reagents were commercially available and used as supplied without further purification.

General Experimental Procedures

Nuclear magnetic resonance (NMR) spectra were obtained in DMSO-$D_6$ or $CDCl_3$ with a Varian 400 MHz spectrometer. All polymers were characterized by $^1$H-NMR and gel permeation chromatography (GPC) (see below) at every step of the synthesis.

UV-Vis Spectrophotometer.

UV/Vis absorption spectra were recorded on an Aminco/OLIS UV-Vis spectrophotometer or by scanning between 350-750 nm with a SpectraMax Plus spectrophotometer (Molecular Devices). The absorbance peak at 430 nm was attributed to complex formation between DFO and Fe (III).

Transmission Electron Microscopy.

TEM images of nanogels were taken on a Tecnai TF-12 instrument with an acceleration voltage of 120 kV. Sample was prepared by air-drying a drop of 0.01 mg/mL nanogel suspension on copper grid.

Dynamic Light Scattering.

DLS measurements were collected on a Zetasizer Nano ZS (Malvern Instruments, UK) and analyzed with Zetasizer software v7.10. For DLS measurements, nanogels were suspended in $dH_2O$ at about 1 mg/mL. The cumulant analysis was used to calculate the z-average diameter and polydispersity index (PDI). Measurements were conducted on three batches of samples and results are reported as mean±standard deviation (SD). Prior to measurement the nanogel solutions were clarified by filtering through Millipore membranes with a 0.45 μm pore size.

Gel Permeation Chromatography.

Aqueous phase GPC was used to measure the apparent molecular weight changes of oxNG-DFO. GPC data acquisition was conducted on a Shimadzu UFLC system equipped with Shodex OHpak SB-806M HQ column (8.0×300 mm), and eluted with MilliQ water at a flow rate of 0.5 mL/min. Nanogels were detected with a refractive index detector (RID). GPC data was analyzed with Shimadzu LCsolution GPC postrun software.

Ferrocene (Fc) and DFO Content Measurement.

Atomic absorption spectroscopy (AAS) was used to indirectly determine Fc and DFO content in nanogels.

Fc Content Measurement:

Typically, 1 mg of oxNG-DFO was dissolved in 1 mL $dH_2O$. Iron, Fe(III), concentration was measured by AAS on a GBC 932AA instrument. The Fc content in oxNG-DFO can then be calculated by the following equation:

$$Fc \text{ content} = \frac{W_{Ec}}{W_{oxNG\text{-}DFO}} = Fc \text{ Content} = \frac{c \times M_w \times V}{W_{oxNG\text{-}DFO}}$$

where c is the concentration of Fe(III) determined by AAS (in the unit of mol/L), which should equal the concentration of Fc; $M_W$ is the molecular weight of Fc (186 g/mol); V is the volume of the solution; $W_{oxNG\text{-}DFo}$ is the concentration of oxNG-DFO (mg/mL).

DFO Content Measurement:

Typically, excess amount of $FeCl_3$ was added to 1 mg/mL nanogel solution and incubated overnight. After the chelation reaction was complete, the mixture was extensively dialyzed (MWCO 10,000) in deionized water to remove excess Fe(III) ions. After dialysis, the final volume in solution was measured to account for the dilution effect during dialysis and Fe concentration was measured by AAS on a GBC 932AA instrument. Assuming that DFO chelates Fe(III) in a 1:1 molar ratio and presence of one Fc moiety in each β-CD cavity, the DFO content in oxNG-DFO can be calculated from the following equation:

$$DFO \text{ Content} = \frac{W_{DFO}}{W_{oxNG\text{-}DFO}}$$
$$= Fc \text{ total Content} - Fc \text{ Content}$$
$$= \frac{c \times M_w \times V_f}{W_{oxNG\text{-}DFO} \times V_f} - Fc \text{ Content}$$

where c is the total concentration of Fe(III) determined by AAS (in the unit of mol/L), which according to our assumption should equal the concentration of DFO; $M_W$ is the molecular weight of DFO (560 g/mol); $V_f$ is the final volume after dialysis; $V_i$ is the initial volume of the solution before dialysis; $W_{oxNG\text{-}DFO}$ is the concentration of oxNG-DFO (mg/mL).

Cytotoxicity.

Mouse macrophage/monocyte cell line, J774A.1, was purchased from American Type Culture Collection (ATCC). Cells were seeded in 96-well plates at a density of 3,000 cells/well, cultured at 37° C., 5% $CO_2$ with DMEM complete medium (supplemented with 10% (v/v) heat-inactivated FBS, 100 I.U./mL penicillin and 100 μg/mL streptomycin), and allowed to settle for 24 h. Cells were then treated with DFO or oxNG-DFO at equivalent DFO concentrations of 1 mM prepared by 1:3 serial dilutions.

Cell viability was measured with the metabolism-based resazurin assay. Briefly, the substrate resazurin was dissolved in cell culture medium at a concentration of 44 μM, added to each well (100 μl) and incubated at 37° C. for 4 h. The fluorescence was measured with excitation at 560 nm and emission at 590 nm, on a SpectraMax Gemini EM microplate reader. Readings from the wells without cells were used as $E_{blank}$, and the readings from control cells without treatment ($E_{control}$) represented 100% cell viability. The viability of treated cells at different concentrations can be calculated by the following equation:

$$\text{Cell viability} = 100 \times \frac{E_{sample} - E_{blank}}{E_{control} - E_{blank}} \%$$

Similarly, cytotoxicity was also evaluated in iron-overloaded J774A.1 cells as described above. Cells were iron overloaded for 24 h prior to the DFO cytotoxicity study by incubation with culture medium containing 100 μM ferric ammonium citrate (FAC) (cells>80% viable with FAC incubation, data not shown).

Ferritin Reduction Assay in Iron Overloaded J774A.1 Cells.

J774A.1 cells were seeded in 6-well plates at a density of 30,000 cell/well and allowed to settle for 24 h at 37° C., 5% $CO_2$ with DMEM complete medium before treatment. The cells were treated with 100 μM FAC (added to DMEM complete medium) for 24 h to induce iron overload. Subsequently, cells were washed with PBS and treated with DFO or oxNG-DFO at both 10 μM and 50 μM for 48 h. Control group A cells were not iron-overloaded with FAC; cells in control group B were iron-overloaded with FAC but not treated with DFO or oxNG-DFO. After 48 h incubation with DFO or oxNG-DFO, cells were lysed with cell lysis buffer (150 mM NaCl, 10 mM Tris, 1% Triton X-100 and protease inhibitor cocktail, pH 7.4) and total protein concentration was measured with the BCA protein assay kit. Cellular ferritin concentration was measured with a mouse ferritin ELISA kit. The results are plotted as the ratio of ng of ferritin per µg total protein concentration.

Statistical Analysis.

Statistical analysis was performed with GraphPad Prism 5.0 software. Statistical significance between groups was assessed with Student's t-test; a two-tailed $p<0.05$ was considered statistically significant.

Example 1: Preparation of Redox-Sensitive Bulk Gels (rBG) and Nanogels (rNG)

A. Synthesis of the Gel Monomers: Fc-AAm, βCDm, and DFOm

1. Synthesis and Characterization of Fc-AAm

Scheme 1 shows a synthetic scheme used to prepare ferrocenyl acrylamide monomer (Fc-AAm, 3).

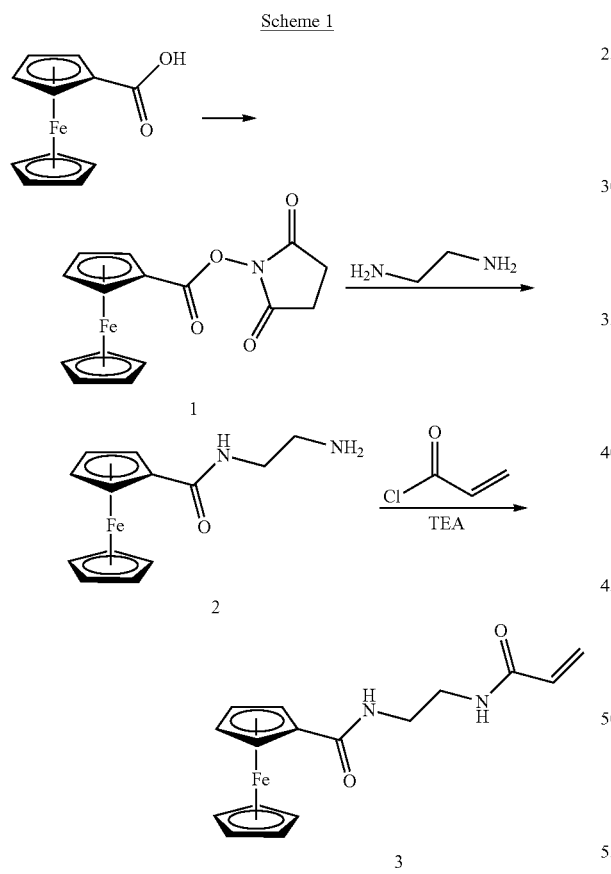

Preparation of Fc-NHS:

Fc-NHS was synthesized following a reported method (C. Feng, G. L. Lu, Y. J. Li, X. Y. Huang, *Langmuir* 2013, 29, 10922-10931). Fc-COOH (49.9 mg, 0.22 mmol), EDC (58.6 mg, 0.32 mmol), and NHS (37.5 mg, 0.32 mmol) were dissolved in dry DCM (5 mL). The reaction mixture was stirred for 24 h at room temperature. After filtering, the filtrate was concentrated and dried in vacuo. Fc-NHS was obtained by silica gel column chromatography (dichloromethane:methanol=10:1) as an orange solid.

$^1$H-NMR (400 MHz, CDCl$_3$, 298° K): δ=2.93 (s, 4H, —CH$_2$—CH$_2$—), 4.42 (s, 5H, Cp), 4.60 (m, 2H, Cp), 4.97 (m, 2H, Cp).

Preparation of Fc-CONH—(CH$_2$)$_2$—NH$_2$:

Fc-NHS (32.7 mg, 0.10 mmol) was dissolved in 5 mL of DCM; EDA (1 mL, 14.80 mmol) and TEA (1 mL, 7.20 mmol) were also dissolved in 5 mL of DCM. The Fc-NHS solution was added dropwise into the EDA/TEA solution and the reaction mixture was stirred overnight at room temperature. After filtering the reaction, the filtrate was concentrated, followed by washing with water and brine, and dried over Na$_2$SO$_4$. The DCM layer was diluted with 50 mL of hexane to precipitate a solid product, which was collected via centrifugation and dried in vacuo to obtain Fc-CONH—(CH$_2$)$_2$—NH$_2$ as a yellow powder.

Preparation of Fc-AAm:

Fc-CONH—(CH$_2$)$_2$—NH$_2$ (33.7 mg, 0.12 mmol) from the previous step and TEA (25 µL, 0.18 mmol) were dissolved in THF (2.5 mL). Acryloyl chloride (12 µL, 0.15 mmol) was added dropwise to the THF solution while cooling in an ice bath. The reaction mixture was stirred for 2 h at room temperature. The solution was filtered, and the filtrate was concentrated and dried in vacuo. Silica gel column chromatography (dichloromethane:methanol=9:1) of the resulting product provided Fc-AAm was obtained as an orange solid.

$^1$H NMR (400 MHz, CDCl$_3$, 298° K): δ=3.56 (t, 4H, Fc-CONH—(CH$_2$)$_2$—NHCO—), 4.18 (s, 5H, Cp), 4.35 (t, 2H, Cp), 4.71 (t, 2H, Cp), 5.66-5.70 (m, 1H, olefin), 6.13-6.20 (m, 1H, olefin), 6.30-6.35 (m, 1H, olefin), 6.65-6.75 (d, 2H, amide).

2. Synthesis and Characterization of Mono-6-(Allyl Amino)-β-Cyclodextrin (βCDm)

Scheme 2 below shows the synthetic route used to prepare mono-6-(allyl amino) β-cyclodextrin (βCDm).

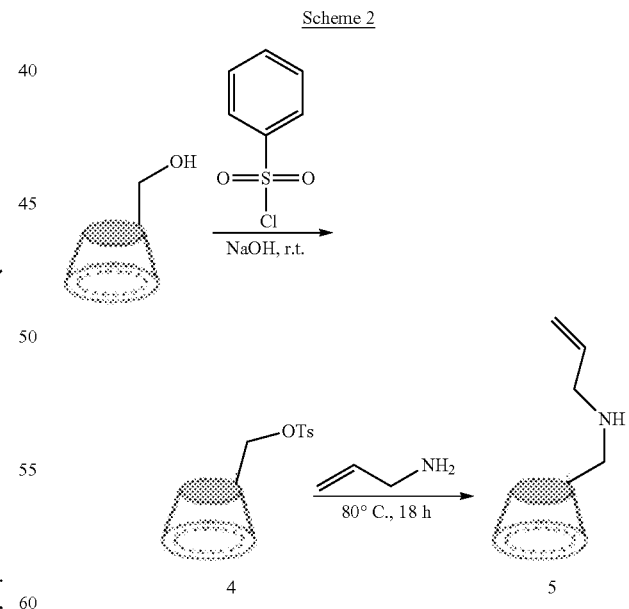

Preparation of the Mono-6-OTs-β-cyclodextrin:

Mono-6-OTs-β-CD was prepared as previously reported (A. C. Feng, Q. Yan, H. J. Zhang, L. Peng, J. Y. Yuan, *Chem Commun* 2014, 50, 4740-4742). Dry β-CD (6 g, 5.27 mmol) was dissolved in 50 mL of water. Sodium hydroxide (0.657 g, 16.43 mmol) was dissolved in 2 mL of water and added dropwise into the β-CD solution. The mixture was cooled in an ice bath. Subsequently, to the solution 3 mL of p-toluenesulfonyl chloride (1.21 g, 6.35 mmol) in acetonitrile was added in small portions under vigorous stirring over 10 min. The resulting suspension was stirred for 2 h at room temperature and then quickly filtered. The filtrate was refrigerated overnight at 4° C. The resultant precipitate was filtered off, washed three times with water and acetone and recrystallized from hot water three times. The final product was dried under vacuum.

$^1$H NMR (400 MHz, DMSO-d6, 298° K): δ=2.43 (s, 3H, Ph-CH3), 3.15-3.40 (m, H2, H4 overlap with water), 3.40-3.75 (m, 25H, H3, H5 and H6 CyD), 4.15 (m, 1H, H5' CyD), 4.30 (m, 2H, H6' CyD), 4.35-4.50 (m, 6H, OH6 CyD), 4.71-4.80 (m, 7H, H1 CyD), 5.59-5.83 (m, 14H, OH2 and OH3 CyD), 7.43 (d, 2H, Ph), 7.77 (d, 2H, Ph).

Preparation of the monomer, Mono-6-(allyl amino)-β-cyclodextrin:

Mono-6-OTs-β-CD (1.97 g, 1.53 mmol) prepared as in the previous step was reacted with excess amount of allylamine (30 mL, 306 mol) in the presence of a small amount of

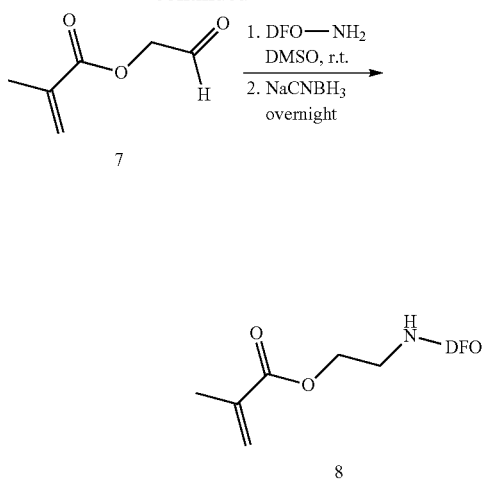

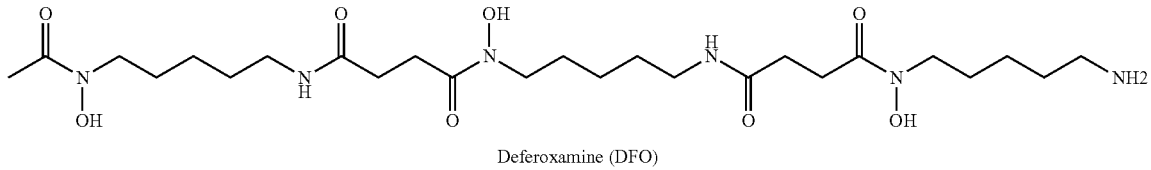 [SMILES: CC(=O)N(O)CCCCCNC(=O)CCC(=O)N(O)CCCCCNC(=O)CCC(=O)N(O)CCCCCN]

Deferoxamine (DFO)

1,4-dihydroxybenzene at 80° C. for 18 h. After the reaction was completed, the resulting solution was cooled to room temperature and diluted with MeOH (30 mL). When acetonitrile (100 mL) was added, a colorless solid precipitated. The precipitate was collected by centrifugation and repeatedly dissolved in MeOH and poured into a large amount of acetonitrile several times. After filtering and drying under high vacuum, the final product was obtained.

$^1$H NMR (400 MHz, DMSO-d6, 298° K): δ=3.12 (m, 2H, CyD-NH—CH2-), 3.21-3.72 (m, H2, H3, H4, H5 and H6 CyD); 4.62 (br, 6H, OH6 CyD), 4.75 (s, 7H, H1CyD), 4.93-4.99 (d, 1H, olefin), 5.05-5.16 (d, 1H, olefin), 5.65-5.71 (br, 14H, OH2 and OH3 CyD), 5.75-5.85 (m, 1H, olefin).

3. Synthesis and Characterization of DFO-Monomer (DFOm)

Scheme 3 Shows the Synthetic Route Used to Prepare DFO-Monomer.

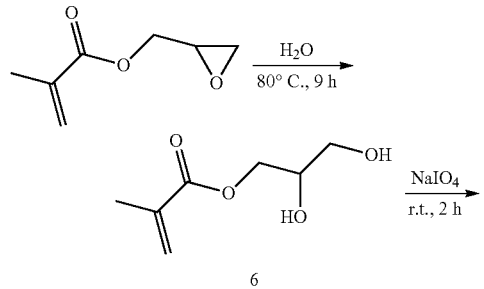

Preparation of 1-Glycerol Methacrylate (6):

1-Glycerol methacrylate (aka, hydrolyzed glycidyl methacrylate, hGMA) was synthesized by hydrolysis of GMA following a reported method L. P. D. Ratcliffe, A. J. Ryan, S. P. Armes, Macromolecules 2013, 46, 769-777. Glycidyl methacrylate (4.96 g, 35 mmol) was added to water (44.78 g, 10% w/w solution) in a round-bottomed flask fitted with a condenser. The top of the condenser was open to the atmosphere during the reaction, for the purpose of allowing oxygen to inhibit the polymerization of monomers. The initial emulsion was stirred for 9 h at 80° C. and eventually became a homogeneous aqueous solution.

$^1$H-NMR (400 MHz, D$_2$O, 298° K): 1.90 (s, 3H, —CH3), 3.56-3.68 (m, 2H, —CH2), 3.72-3.76 (m, 2H, —CH2), 3.94-4.02 (m, 1H, —CH), 4.11-4.28 (m, 2H, —CH2), 4.98-5.04 (m, 1H, —CH), 5.66-5.74 (m, 1H, olefin), 6.09-6.18 (m, 1H, olefin).

Preparation of 2-oxoethyl methacrylate (OEMA) (7):

NaIO$_4$ (1.34 g, 6.26 mmol) was added to 10 mL of hGMA (10% w/w) aqueous solution prepared as in Example 1 above, and the mixture was stirred at room temperature for 2 h. The mixture was extracted with DCM and evaporated under reduced pressure. After filtering, the final product was extracted from water with 10 mL of DCM, followed by drying over Na$_2$SO$_4$. The DCM layer was concentrated and dried in vacuo. The final OEMA product was obtained by silica gel column chromatography (dichloromethane:methanol=1:1) as a colorless oil.

$^1$H-NMR (400 MHz, CDCl$_3$, 298° K): 1.90 (s, 3H, —CH3), 4.74 (s, 2H, —CH2), 5.61-5.75 (m, 1H, olefin), 6.13-6.26 (m, 1H, olefin), 9.69 (s, 1H, —CHO).

Preparation of DFO-Monomer (8):

DFO mesylate (65.7 mg, 0.10 mmol) and OEMA (19 mg, 0.15 mmol) prepared in the previous step were dissolved in 2 mL of DMSO and stirred at room temperature for 4 h.

NaBH₃CN (10 mg, 0.16 mmol) was added to the mixture and stirred overnight. The resultant precipitate was filtered off and the filtrate was added to 20 mL of ether. The precipitate was collected by centrifugation and repeatedly dissolved in MeOH, filtered, and re-precipitated from ether. After drying under high vacuum, DFO monomer (8) was obtained as white solid.

$^1$H-NMR (400 MHz, CDCl₃, 298° K): 1.15-1.5 (m, 18H, —CH₂—), 1.85 (s, 3H, —CH3), 1.91 (s, 3H, —CH3), 2.19-2.28 (m, 2H, —CH₂—NH—), 2.30-2.51 (m, 8H, —CH₂—CO—), 2.51-2.75 (m, 2H, —CH₂—NH—), 2.84-3.00 (m, 4H, —CH₂—NHCO—), 3.25-3.5 (m, 6H, —CH₂—NOH—), 4.12 (t, 2H, —CH2-OCO—), 5.63-5.70 (m, 1H, olefin), 5.94-6.10 (m, 1H, olefin), 7.60-7.75 (br, 3H, —NH), 9.51-9.64 (m, 3H, —OH)

B. Preparation of the Redox Sensitive Cross-Linking Monomer Complex, βCDm:Fc-AAm (a Host-Guest System)

The host guest system of bCDm and FC-AAm was prepared as shown in Scheme 4.

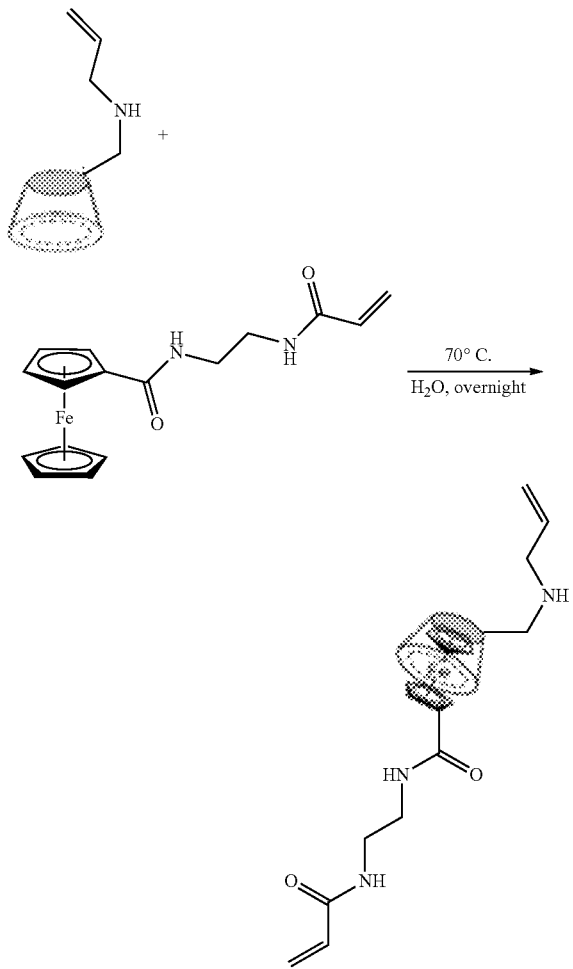

Scheme 4

The prepared βCDm (36 mg, 0.030 mmol) and Fc-monomer (Fc-AAm, 9.8 mg, 0.030 mmol) from step A were mixed in distilled water (1 mL) and stirred at 70° C. overnight, yielding a transparent solution.

C. Preparation and Testing of the Bulk Hydrogels

1. DFO-BG (without Incorporation of Cross-Linking Monomer Complex)

150 mg acrylamide (AAm), 150 mg poly(ethylene glycol) diacrylate (PEG-DA) and 5 mg DFO-monomer (DFOm) was dissolved into 1 mL dH₂O. Next, 11 mg VA-044 (initiator) was added to the solution. The solution was purged with nitrogen gas for 1 h and was then heated at 50° C. overnight to form a gel. The gel was washed repeatedly with water and DMSO to provide DFO-BG. The BG-DFO in water after washing reveals a clear looking gel. BG-DFO incubated in a solution containing excess Fe(III) (5 mg/mL) reveals the gel acquiring a deep red color which is the result of iron chelating to the gel. After iron chelation, BG-DFO:Fe(III) was washed with water and DMSO and immersed in DMSO; the color of the washing solution did not change and indicated that the DFO-monomer was successfully incorporated into the backbone of the gel during polymerization.

2. rBG, without DFOm Incorporated 150 mg of AAm was dissolved into 1 mL aqueous solution of the host-guest crosslinking βCDm:Fc-AAm. Next, 3 mg VA-044 (initiator) was added to the solution. The solution was purged with nitrogen gas for 1 h and was then heated at 50° C. overnight to form a gel. The gel was washed repeatedly with water and DMSO. Visual inspection of the resulting product was consistent with formation of the bulk gel. First, polymerization in the presence of the host-guest crosslinker resulted in a solid yellow colored bulk gel. Second, the resulting rBG was stable in water. Third, when the rBG is incubated in H₂O₂ (5%), the bulk gel completely disappears after 30 min incubation and indicates that the crosslinker was successfully oxidized. Fourth, in the presence of excess Fe(III) (50 mg/mL) which looks dark yellow in color, rBG also oxidizes and turns to a dark green color indicative of successful oxidation of ferrocene. Fifth, about 4 h incubation at RT, rBG incubated in excess Fe(III) solution (50 mg/mL) completely dissolved and the result suggests successful disassembly of rBG into smaller structures due to oxidation of the crosslinker. Thus the strength and concentration of the oxidizing agent plays an important role in the rate of degradation of these rBGs.

D. Preparation of the DFO Nanogel (DFO-NG, without Redox Crosslinking Monomer Added)

The DFO-NG was prepared without a redox cross-linking monomer. 0.79 g AOT and 1.54 g Brij 30 were added to a 100 mL flask. Hexane (43 mL) was added to dissolve the surfactants, then the mixture was stirred and purged with nitrogen. 1 mL of an aqueous solution of monomers, cross-linker, and initiator (typically 0.7 mL H₂O, 150 mg PEG-DA (cross-linker), 150 mg acrylamide (AAm), 5 mg DFO-monomer (DFOm), 11 mg VA-044 (initiator)) was added slowly by syringe to the stirred solution. The solution was stirred until it became clear with a slight bluish color, indicative of emulsion formation. The solution was purged with nitrogen gas for 1 h and was then heated at 50° C. overnight. The hexane was removed under reduced pressure using a rotary evaporator. The resulting particles were washed with ethanol repeatedly until free of surfactants. FIG. 1 shows the UV-Vis spectra of a Fe(III) solution, a nanogel as prepared by the present procedure, and the same nanogel and Fe(III).

E. Preparing Redox-Nanogels rNG, without DFOm added; only the crosslinking bCDm:Fc-AAm The rNG was prepared with a redox cross-linking monomer but no DFOm as shown in Scheme 5.

Scheme 5

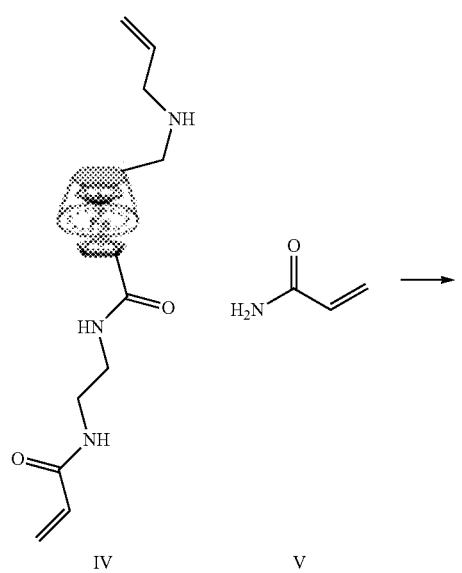

heated at 50° C. overnight. The hexane was removed under reduced pressure using a rotary evaporator. The resulting particles were washed with ethanol repeatedly until free of surfactants.

To test the redox sensitive behavior of the host-guest crosslinking monomer in rNG, a 1 mL sample of the resulting particles in water was mixed with 1 mL of $H_2O_2$ (5% v/v). In the presence of this oxidizing agent, the solution which had initially appeared turbid in water immediately turned clear. This behavior is suggestive of immediate disassembly of rNG into smaller structures.

1. Preparation of the DFO-NG Including Redox-Sensitive Cross-Linking Monomer Complex or DFO-rNG The DFO-rNG can be prepared with a redox-sensitive cross-linking monomer complex (host-guest system) as shown in Scheme 6. Briefly, the nanogel scaffold was prepared by reverse emulsion polymerization. The reverse emulsion was composed of a continuous phase of hexane and a dispersed aqueous phase stabilized by a mixture of two surfactants, AOT and Brij 30, at the same molar ratio of 1:2.4. It will be understood that other ratios may be used to control the size of the resulting gels.

Scheme 6

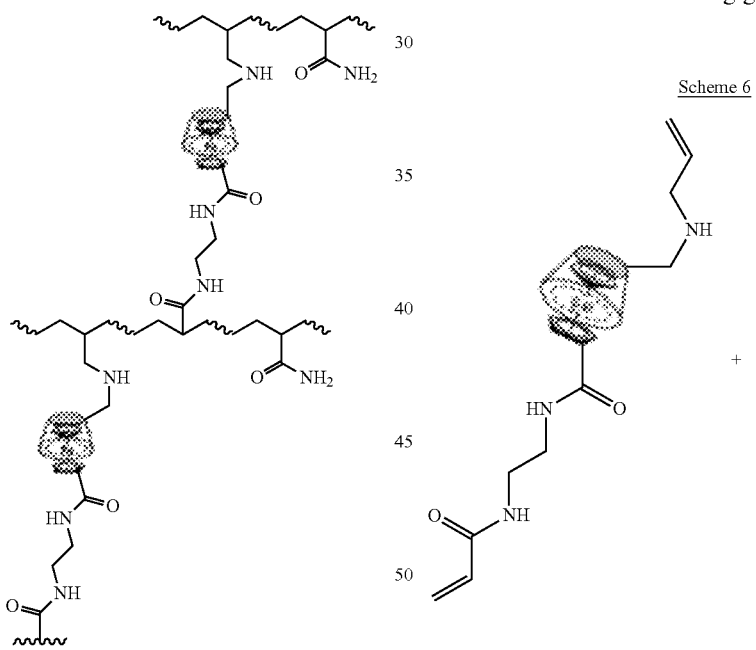

0.79 g AOT and 1.54 g Brij 30 were added to a 100 mL flask. Hexane (43 mL) was added to dissolve the surfactants, then the mixture was stirred and purged with nitrogen. 150 mg acrylamide (AAm) and 11 mg VA-044 (initiator) were added to 1 mL aqueous solution of host-guest crosslinking monomer (bCDm:Fc-AAm). The aqueous solution of monomers, cross-linker, and initiator was added slowly by syringe to the stirred solution containing AOT and Brij 30 detergents. The solution was stirred until it became clear with a slight bluish color, indicative of emulsion formation. The solution was purged with nitrogen gas for 1 h and was then

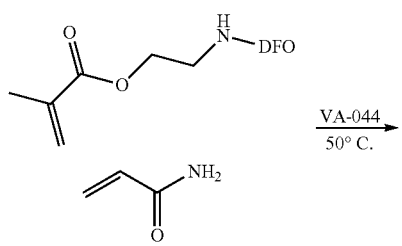

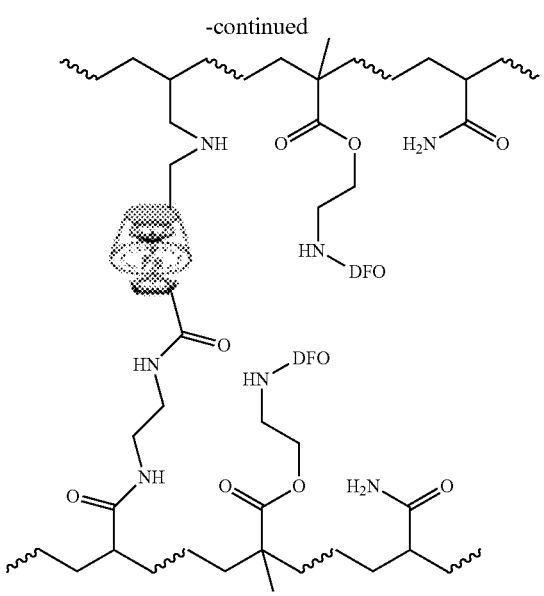

The nanogel scaffold was synthesized via a modified reverse emulsion polymerization method. To a 50 mL round bottom flask, 0.79 g AOT and 1.54 g Brij 30 were added. Next, 22 mL hexane was added to dissolve the surfactants under magnetic stirring at 1000 rpm. The stirring emulsion was purged with nitrogen gas for 1 h to remove dissolved oxygen. Separately, 150 mg acrylamide and varying amounts of DFOm was dissolved into 1 mL aqueous solution of host-guest crosslinker. The precursor solution was purged with nitrogen gas for 1 h and slowly added to the stirring surfactant/hexane solution with the aid of a syringe to form reverse water-in-oil emulsions. Next, 3 mg VA-044 in 50 µl dH$_2$O was added to the mixture and heated at 50° C. overnight to initiate polymerization. When the polymerization was completed, hexane was removed on a rotary evaporator, and the nanogel was precipitated with 25 mL methanol, centrifuged, and washed with ethanol 6× (25 mL each) to remove excess surfactants, initiators, unreacted monomers and cross-linkers. Final nanogels were dialyzed (MWCO 10,000) against dH$_2$O (six changes within 24 h). The final product can be lyophilized to yield a yellow colored solid for prolonged storage. Table 1 shows the various nanogels that were prepared. Both z-average diameter and PDI were measured by DLS in accordance with the general procedures given above.

Example 2: Characterization of Redox-Sensitive Gels

As shown in Table 1, The diameter and PDI of nanogels prepared in Example 1 were similar. Therefore, oxNG2-DFO was selected as a representative nanogel for further analysis.

Figure 2A:
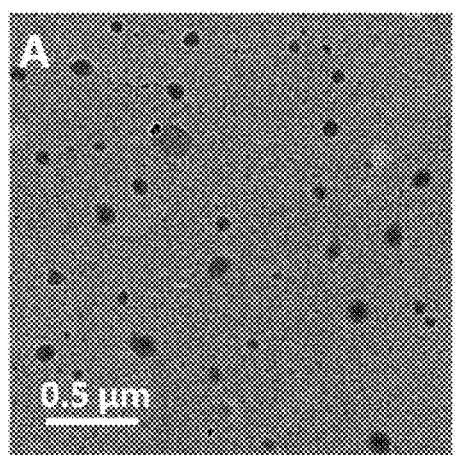
FIG. 2A shows a representative TEM image of oxNG2-DFO nanogels at the 0.5 μm scale.
Figure 2B:
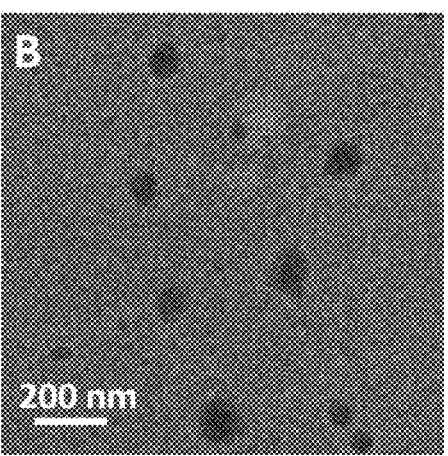
FIG. 2B shows the same at the 200 nm scale.

FIGS. 2A and 2B show representative EM micrographs of oxNG2-DFO. At the 200 nm scale level the oxNG2-DFO averaged about 100 nm (FIG. 2B). This is mailer than the size estimated by DLS and may be attributed to nanogel shrinkage during the preparative process of air-drying TEM samples.

Figure 2C:
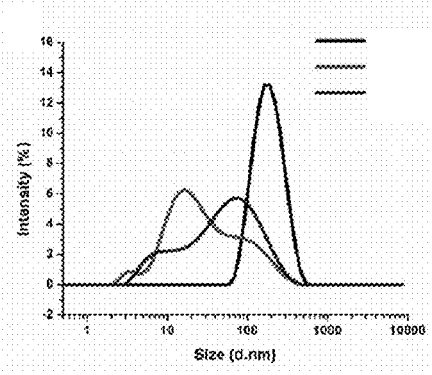
FIG. 2C shows the DLS size distribution of oxNG2-DFO dispersed in $ddH_2O$ (black line, 1), 1% $H_2O_2$ (blue line, 3), and 5% $H_2O_2$ (red line, 2) after 240 h incubation at RT.
Figure 2D:
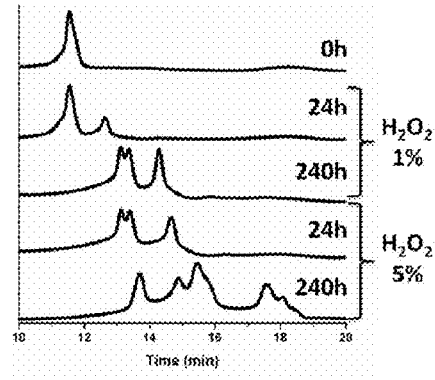
FIG. 2D shows changes in the apparent molecular weight of oxNG2-DFO in the presence of 1% and 5% $H_2O_2$ as monitored by GPC at RT.
Figure 3A:
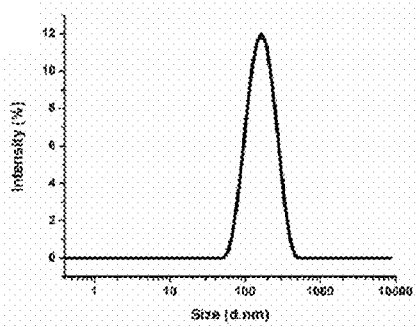
FIGS. 3A and 3B show the DLS size distribution of oxNG2-DFO incubated in dH$_2$O after 24 h and 240 h, respectively, and reveal stable-sized nanoparticles.
Figure 3B:
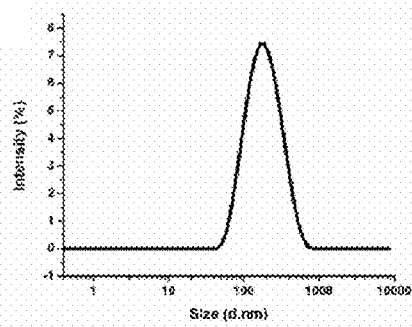
Figure 3C:
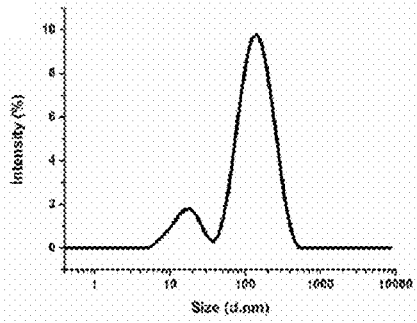
FIGS. 3C and 3D show that oxNG2-DFO incubated in 1% H$_2$O$_2$ and 5% H$_2$O$_2$, respectively, after 24 h reveal increasingly more degradation products in the presence of the oxidizer due to the oxidation-sensitive crosslinker.
Figure 3D:
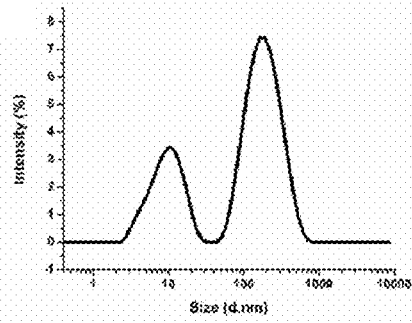

The rate of degradation the rate of degradation of oxNG2-DFO was investigated at three concentrations of H$_2$O$_2$ to simulate different levels of oxidative stress: (a) 0%; (b) 1%; (c) 5%. The kinetics of nanogel degradation was monitored by both DLS and gel permeation chromatography (GPC) up to 240 h (10 days). Although the samples were only capped and not stored under an inert atmosphere during these studies, the nanogels were relatively stable in solution without H$_2$O$_2$ and no significant size changes were observed by DLS after 24 h or 240 h incubations (FIGS. 3A and 3B). On the other hand, evidence of oxNG2-DFO degradation can be clearly observed in the presence of both 1% and 5% H$_2$O$_2$ at an oxidative stress-dependent rate. Z-average diameter of oxNG2-DFO was 136 nm initially but after 24 h incubation in 1% H$_2$O$_2$, a smaller peak at ca. 20 nm appeared (FIG. 3C). Over the course of 240 h, evidence of further degradation became apparent by monitoring the PDI of nanogels which increased from 0.15 to 0.63 (FIG. 2C). Similar to the pattern observed in 1% H$_2$O$_2$, the z-average diameter decreased in 5% H$_2$O$_2$ at 24 h, but at a faster rate than in 1% H$_2$O$_2$ (FIG. 3D) and the PDI increased from 0.15 to 0.79 by the end of the 240 h study (FIG. 2C). The DLS data clearly demonstrates that nanogels exhibit varying rates of degradation proportional to the level of oxidative stress. Degradation patterns for oxNG2-DFO were further monitored by GPC (FIG. 2D). The intact nanogels eluted at 11.4 min, but with increased incubation time this peak disappeared and was replaced by peaks with longer elution times indicative of degradation. Increasing the concentration of H$_2$O$_2$ further increased the degradation rate, as nanogels in 5% H$_2$O$_2$ at 24 h had a similar GPC curve to the nanogels exposed to 1% H$_2$O$_2$ at 240 h. After 240 h in 5% H$_2$O$_2$, more peaks eluting at later times could be observed.

To probe the iron chelating capability of nanogels, UV-Vis absorption was used to confirm the formation of a 1:1 complex between conjugated DFO and ferric iron, Fe(III), by monitoring its characteristic absorption peak at ca. 430 nm. After mixing the solution of oxNG2-DFO (0.5 mg/ml) with FeCl$_3$ (0.5 mg/ml), a distinct clear yellow-brown color

TABLE 1

Figure 4A:
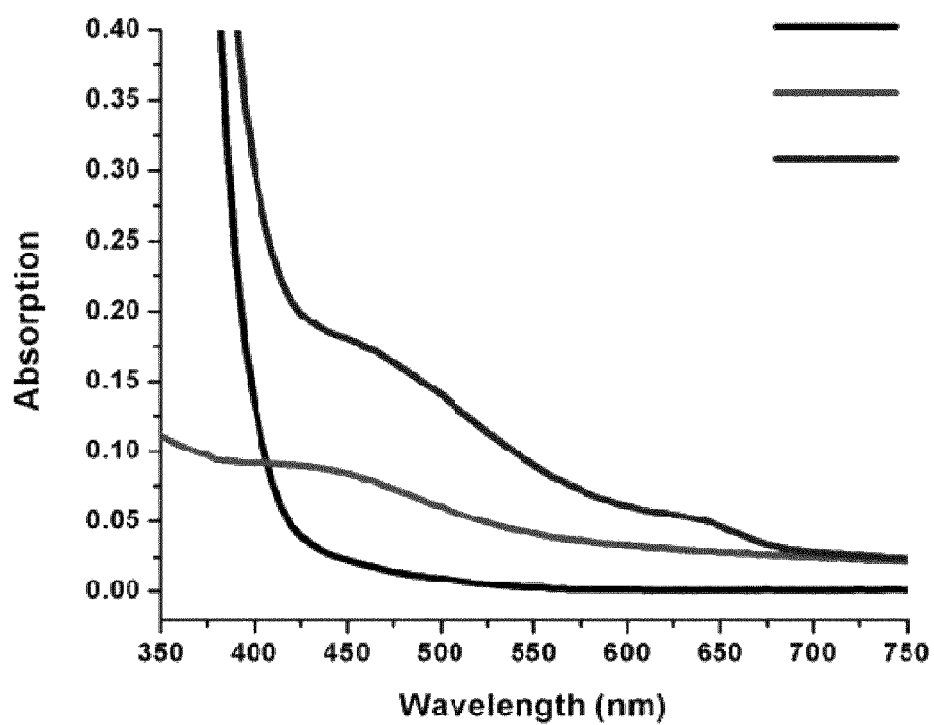
FIG. 4A shows the UV-Vis absorption spectrum of Fe(III) in solution (black line, 1), oxNG2-DFO in solution (red line, 2), and oxNG2-DFO in the presence of Fe(III) (blue line, 3). After spin filtering through a centrifugal filter unit (MW cut-off 10,000), the clear filtrate and yellow-brown (nanogel-iron chelate) concentrate were examined.
Figure 5:
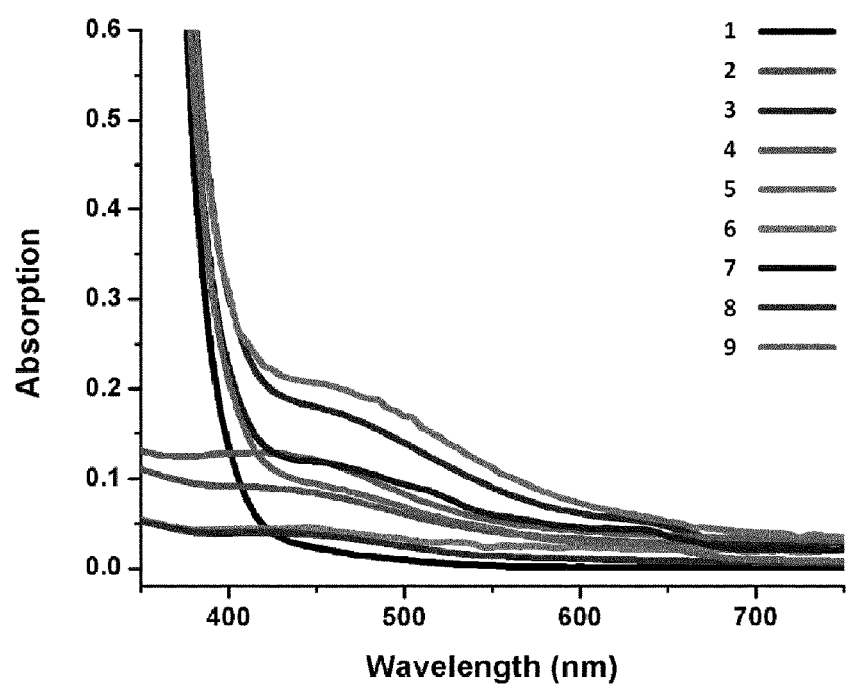
FIG. 5. UV-Vis absorption spectrum of Fe(III) (line 1) or nanogels alone reveal only minimal absorbance at ca. 430 nm: oxNG1-DFO (line 4), oxNG2-DFO (line 2), oxNG3-DFO (line 6), oxNG4-DFO (line 8). In contrast, UV-Vis absorption spectrum of nanogel-iron chelates in solution reveal a strong absorption peak at ca. 430 nm: oxNG1-DFO/Fe(III) (line 5), oxNG2-DFO/Fe(III) (line 3), oxNG3-DFO/Fe(III) (line 7), and oxNG4-DFO/Fe(III) (line 9). The increasing absorbance at 430 nm correlates with more complex formation and indicates that DFO at various levels was indeed successfully conjugated to the nanogels.

| | Host-guest crosslinker (mg) | AAm (mg) | VA-044 (mg) | DFO Monomer (mg) | Molar ratio | Z-average diameter (nm) | PDI |
|---|---|---|---|---|---|---|---|
| oxNG1-DFO | 45.7 (1:1) | 150 | 3 | 100 | 1:75:0.3:5 | 148 ± 13 | 0.14 = 0.03 |
| oxNG2-DFO | 45.7 (1:1) | 150 | 3 | 50 | 1:75:0.3:2.5 | 136 ± 9 | 0.15 = 0.02 |
| oxNG3-DFO | 45.7 (1:1) | 150 | 3 | 25 | 1:75:0.3:1.25 | 131 ± 16 | 0.19 = 0.04 |
| oxNG4-DFO | 45.7 (1:1) | 150 | 3 | 10 | 1:75:0.3:0.5 | 141 ± 10 | 0.16 = 0.03 | immediately forms, which is indicative of nanogel-iron chelates. This was further verified by UV absorbance measurements of oxNG2-DFO/Fe(III) chelates (FIG. 4A). With increasing DFO content in the nanogel series prepared, a deeper yellow-brown color and higher absorbance measurements at 430 nm (FIG. 5) were observed, confirming that DFO was indeed successfully incorporated into the scaffold due to formation of increasing iron-DFO complexes.

Figure 4B:
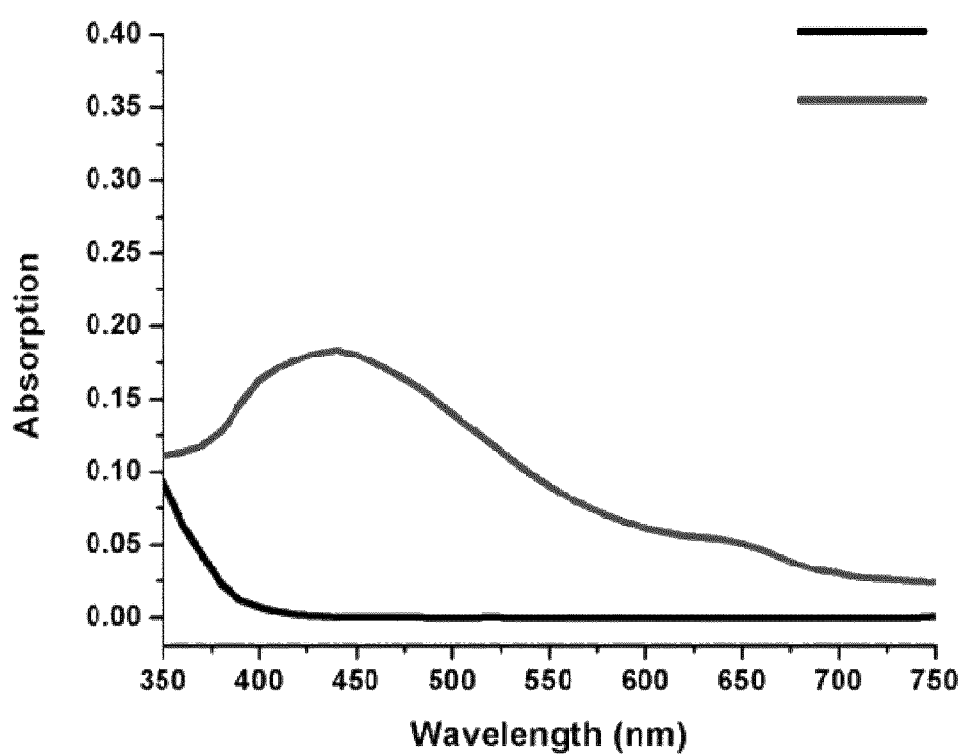
FIG. 4B shows the UV-Vis absorption spectrum of the concentrate displays strong absorption at ca. 430 nm (red line, 2) and no absorption for the filtrate (black line, 1) after extensive washing with the centrifugal filtration unit.

To further verify that DFO was indeed conjugated to nanogels and not just entrapped, the oxNG2-DFO/Fe(III) mixture was washed extensively with a centrifugal filtration unit (MWCO 10,000) and both the recovered oxNG2-DFO/Fe(III) concentrate and the filtrate were collected. Any free DFO/Fe(III) complex in the mixture would have passed through the filter into the filtrate, but the yellow-brown colored suspension containing chelates remained in the concentrate while the clear solution containing excess iron passed through. UV absorbance measurements further confirmed these results. As shown in FIG. 4B, the absorption peak at 430 nm was still observable in the recovered yellow-brown solution even after extensive washing but no absorption peak at 430 nm was detected in the filtrate, confirming that DFO was conjugated to the nanogel scaffold.

Atomic absorption spectroscopy (AAS) can be used to directly measure the concentration of iron chelated to nanogels and can simultaneously indirectly measure the percentage of DFO present because DFO binds stoichiometrically with iron at a 1:1 ratio on the order of $10^{31}$ $M^{-1}$. For this assay, excess $FeCl_3$ was incubated with nanogels overnight, and free iron was removed by extensive dialysis. The DFO conjugation levels can be calculated based on known initial and final iron measurements in the sample according to the general procedures given above. Results for all nanogels are summarized in Table 2, with a w/w DFO conjugation level ranging from 2.69 to 16.49%.

TABLE 2

|  | Fe (%) | Fe (w/w) | DFO (%) | DFO (w/w) |
| --- | --- | --- | --- | --- |
| oxNG1-DFO | 66.62 | 2.99 | 35.64 | 16.49 |
| oxNG2-DFO | 59.61 | 2.86 | 49.32 | 12.21 |
| oxNG3-DFO | 64.26 | 3.27 | 45.21 | 5.92 |
| oxNG4-DFO | 55.81 | 3.00 | 48.60 | 2.69 |

Although DFO is one of the oldest FDA approved chelators for treatment of iron overload conditions, it possesses undesirable cytotoxic effects and has even been investigated as an anticancer drug in clinical trials for advanced hepatocellular carcinoma. The cytotoxicity of free DFO and oxNG2-DFO was compared in J774A.1 mouse monocyte/macrophage cells as well as those that had been iron-overloaded with 100 μM ferric ammonium citrate (FAC). J774A.1 macrophage cells were selected for evaluation because excess iron tends to accumulates first in macrophages for storage in ferritin and hemosiderin, so they play an important role in recycling iron under increased catabolism of erythrocytes, a common symptom of anemia-related blood disorders. If iron-overloaded patients are not treated with iron chelation therapy, the continuous supply of surplus iron accumulating with each blood transfusion can eventually overload macrophages and spill into the bloodstream in the form of reactive non-transferrin bound iron (NTBI), resulting in irreparable damage to hepatic cells and other critical organs.

Figure 6A:
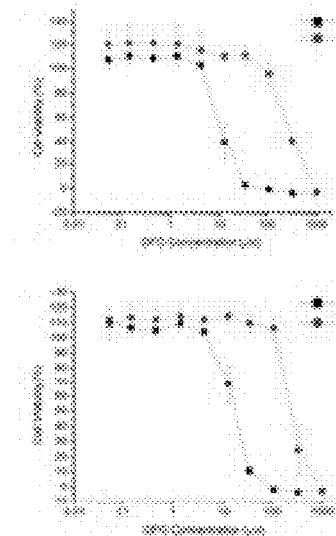
FIG. 6A shows the cytotoxicity of free DFO (black square) and oxNG2-DFO (red circle) in normal J774A.1 cells
Figure 6B:
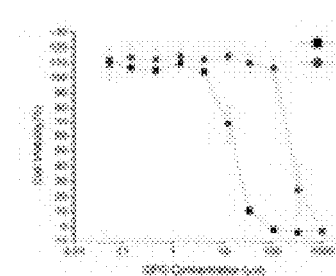
FIG. 6B shows the cytotoxicity in iron-overloaded J774A.1 cells after 48 h incubation; a representative set of data is shown for oxNG2-DFO where each data point is presented as the mean±SD (n=3).

To evaluate the cytotoxicity of the nanogels, cells in complete DMEM medium were treated with equivalent amounts of free DFO or oxNG2-DFO ranging from 0.05-1000 μM and allowed to incubate for 48 h prior to evaluating cytotoxicity with a metabolism-based resazurin assay. As shown in FIG. 6A, free DFO inhibited 50% viability of normal J774A.1 cells at concentration as low as ca. 10 μM, which is comparable to a previous cytotoxicity report in HUVEC cells (M. I. ul-haq, J. L. Hamilton, B. F. L. Lai, R. A. Shenoi, S. Norte, I. Constantinescu, H. A. Leitch, J. N. Kizhakkedathu, *Acs Nano* 2013, 7, 10704-10716). However, oxNG2-DFO was 30-fold less toxic compared to free DFO, with 50% cell viability observed at ca. 300 μM. In FIG. 6B, similar results were obtained in iron-overloaded J774A.1 cells; free DFO inhibited 50% cell viability at ca. 15 μM whereas it took ca. 300 μM oxNG2-DFO to inhibit 50% cell viability. The results demonstrate that conjugating DFO to the nanogels can reduce the cytotoxicity of the chelator.

Figure 6C:
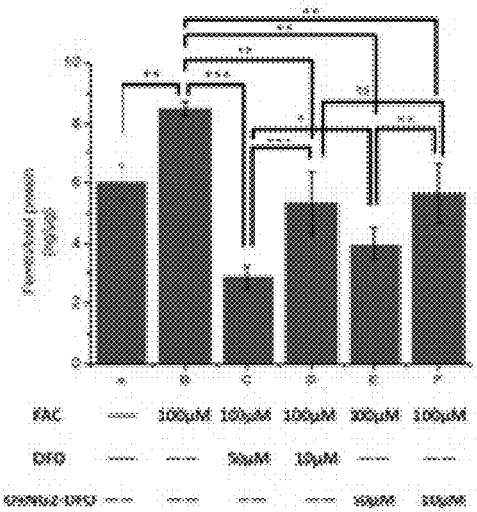
FIG. 6C shows the results of a ferritin reduction assay to monitor iron chelation efficacy of DFO and oxNG2-DFO in iron-overloaded J774A.1 cells. Iron overload was induced by 24 h incubation with 100 μM FAC. Cells were then treated with DFO or oxNG2-DFO at 10 μM or 50 μM for 48 h. Cellular ferritin level was measured by a mouse ferritin ELISA assay. Results are normalized to total protein (ng/μg) and presented as mean±SD (n=3). "ns" means the difference was not significant. * p<0.05,  p<0.01, * p<0.001.

To show that the present nanogels can safely chelate excess intracellular iron, J774A.1 macrophage cells were iron-overloaded with 100 μM FAC for 24 h. The addition of iron in cells results in increased ferritin expression level. It was found that 100 μM FAC treatment of cells for 24 h offered the best balance for inducing increased cellular ferritin expression without affecting cell viability (>80% cells were still viable, data not shown). As shown in FIG. 6C, 100 μM FAC treatment increased cellular ferritin expression from 6.01 ng/μg total protein to 8.51 ng/μg (p<0.01). Subsequently, iron-loaded cells were treated for 48 h with 10 μM or 50 μM free DFO or equivalent oxNG2-DFO. Free DFO administered at 10 μM was able to reduce cellular ferritin level from 8.51 ng/μg total protein to 5.33 ng/μg total protein (37.4% decrease, p<0.01), and even further to 2.84 ng/μg total protein (66.6% decrease, p<0.001) at 50 μM. Treatment with oxNG2-DFO administered at the equivalent of 10 μM DFO decreased ferritin level from 8.51 ng/μg total protein to 5.66 ng/μg total protein (33.5% decrease, p<0.01), and to 3.63 ng/μg total protein (57.3% decrease, p<0.01) at the equivalent dose of 50 μM DFO.

At the lower dose of 10 μM, both free DFO and oxNG2-DFO had similar treatment effects (ns) with ferritin returning to non-iron overloaded control baseline level (FIG. 6C). At the higher dose of 50 μM treatment, ferritin decreased below normal baseline level for both treatments but this effect was less pronounced with oxNG2-DFO compared to free DFO (p<0.05). Although both 10 μM DFO and equivalent oxNG2-DFO returned iron-overloaded cells to control baseline ferritin levels, there was a drastic difference in cytotoxicity and safety between oxNG2-DFO (>100% cells were viable) and DFO (ca. 50% cells viable) (FIG. XXM2B). At 50 μM concentration, the cytotoxicity of DFO was even more pronounced, with <50% cells viable compared to >100% cell viability with oxNG2-DFO (FIG. XXM2B). The difference can likely be attributed to a combination of iron chelation and cytotoxic properties. For example, a critical difference between free DFO and oxNG2-DFO may relate to the role excess iron plays as a catalyst in the production of ROS. As the rate of oxNG2-DFO degradation correlates directly with oxidative stress levels, the nanogel can respond to its environment and only expose DFO as needed rather than removing too much iron too fast, as is the case with free DFO. As oxidative levels begin to normalize again with reduction of the chelatable iron pool, degradation of the nanogel and hence iron chelation correspondingly slows down. For intracellular chelation, it is undesirable to chelate too much iron from cells since it is a critical cofactor for many enzymes responsible for maintaining cellular function. Therefore, oxNG2-DFO is not only as effective a chelator as free DFO in reducing cellular ferritin level, but also a much safer choice for iron chelation due to its ability to sense intracellular oxidation levels.

Example 3: Preparation and Characterization of Hydrolyzable DFO-Conjugated Nanogels (hNG-DFO)

A hydrolyzable DFO-conjugated nanogel of the present technology may be prepared according to Scheme 8 below.

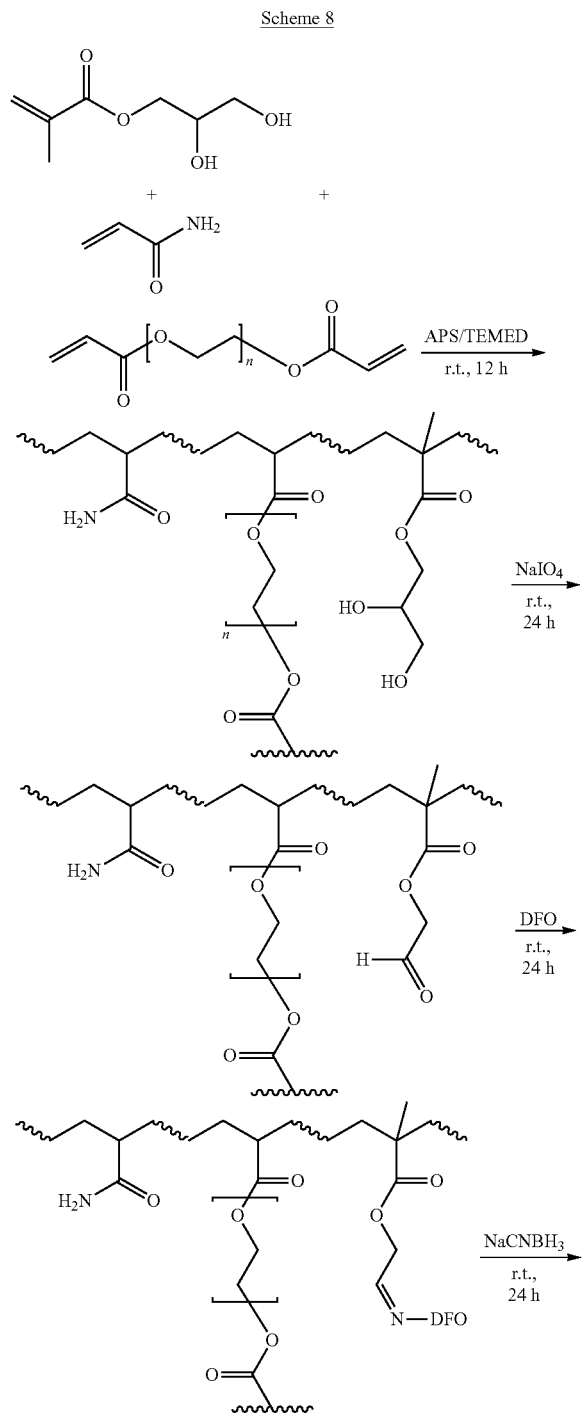

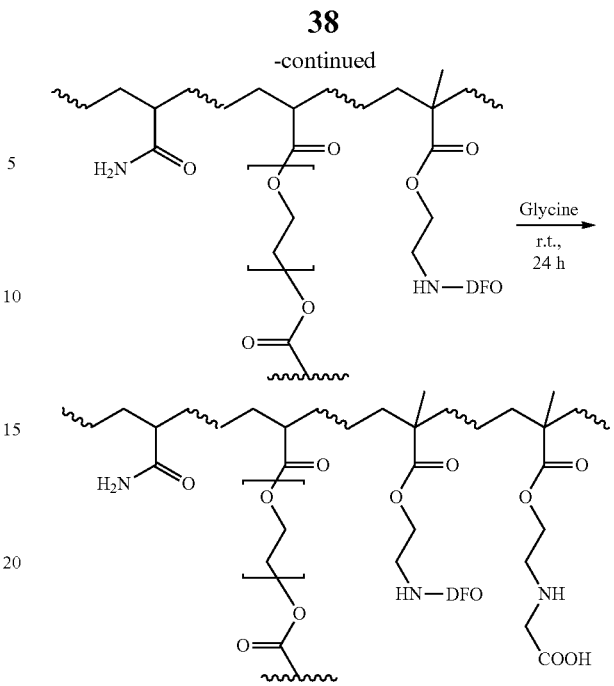

Preparation of Hydrolyzable Nanogels (hNG)

Hydrolyzable DFO-conjugated particles are prepared through a reverse emulsion polymerization process. In one illustrative procedure, 1 g AOT and 2 g Brij 30 were weighed into a 100 mL round bottom flask and dissolved with 24.4 mL hexane (16 g) while stirring with a magnetic stir bar at 1500 rpm. Next, 50 mg AAm, 56 mg hGMA (prepared as above), and 5 mg PEG-DA (mole ratio of 100:50:1) were dissolved in 889 µl ddH$_2$O to a final aqueous weight of 1 g. The aqueous solution was then slowly added to the hexane mixture to form a reverse water/oil emulsion. With stirring, the water/oil emulsion was purged with nitrogen gas for 20 minutes to remove any dissolved oxygen. Polymerization was initiated by adding 100 µL TEMED and 100 µL 15% APS solution sequentially to the emulsion and the reaction was allowed to continue for 16 h at room temperature (22° C.). At the end of polymerization, a rotary evaporator was used to remove the hexane under reduced pressure; the resulting hNGs were precipitated in 50 mL ethanol and washed with ethanol four more times (each with 50 mL ethanol) to remove excess surfactants, initiators, and unreacted monomers and cross-linkers. After the final wash, hNGs were allowed to dry under vacuum. This procedure yielded 100 mg of solid hNGs.

Preparation of Hydrolyzable DFO-Conjugated Nanogels (hNG-DFO)

Figure 7:
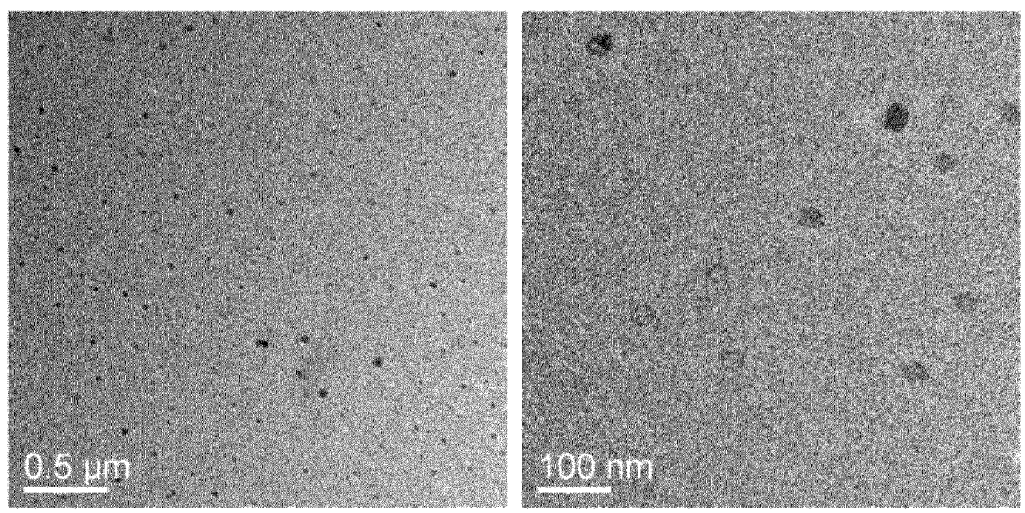
FIG. 7 shows the tunneling electron microscope (TEM) images of an illustrative embodiment of hNG-DFO at 0.5 μm and 100 nm scales (see Example 1).

To conjugate DFO to the hNG, dried hNG was suspended in 10 mL ddH$_2$O followed by addition of 100 mg NaIO$_4$. The solution was stirred for 24 h at room temperature, and then dialyzed (molecular weight cutoff (MWCO), 10 kD) against ddH$_2$O for 24 hours with frequent water changes. Next, 275 mg DFO (about 1.2:1 molar ratio to aldehyde groups) was added to the hNG suspension and stirred for 24 h, resulting in DFO conjugation to the scaffold via Schiff formation which was then reduced by adding 100 mg NaCNBH$_3$ to the mixture and stirred for another 24 h. Any remaining aldehyde groups on hNGs that may not have conjugated to DFO were capped by the addition of 100 mg glycine and stirred for 24 h. The mixture was dialyzed (MWCO, 10 kD) against ddH$_2$O for 3 days to yield pure hNG-DFO. These hNG-DFOs can be freeze-dried to generate a white solid for long-term storage Physical Characterization of hNG-DFO Both Dynamic Light Scattering (DLS) and zeta-potential measurements were conducted with a Zetasizer Nano-ZS (Malvern Instruments). Sample size is reported as the Z-average diameter along with corresponding polydispersity index (PDI); a PDI<0.2 is considered a narrow size distribution of particles. For zeta-potential measurements, dried nanogel powder was dissolved in 10 mM Tris-HCl buffer (pH 7.0) at 2 mg/mL concentration and 800 µL sample was added to a capillary cell. The zeta-potential was determined by the instrument from the measurement of electrophoretic mobility in solution and calculated using the Henry equation. Transmission Electron Microscopy (TEM) images of nanogels were taken with a Tecnai TF-12 instrument at an acceleration voltage of 120 kV. The sample was prepared by air-drying a drop of 0.01 mg/mL nanogel suspension on copper grid prior to imaging. FIG. 7 shows the TEM images of hNG2-DFO particles at 0.5 µm and 100 nm scales. The dark spots are hNG-DFO particles.

Determining DFO Conjugation Levels to hNGs

Two different methods, UV-Vis spectroscopy and atomic absorption spectroscopy (AAS), were used to determine the DFO content in hNG. In the UV-Vis spectroscopy method, an excess amount of $FeCl_3$ was added to a 2 mg/mL hNG-DFO solution, and the absorption at 430 nm corresponding to iron chelation to DFO was measured (see FIG. 8). When this absorbance remained constant in the presence of increasing amounts of iron, it was assumed that 100% hNG-DFO chelation to $Fe^{3+}$ had been reached. DFO % conjugation level to the various hNGs was calculated by using a molar absorptivity coefficient of 2300 $M^{-1}$ $cm^{-1}$.

In the AAS method, an excess amount of $FeCl_3$ was chelated to 2 mg/mL hNG-DFO solution and allowed to incubate for 1 hour at room temperature. The mixture was then dialyzed (MWCO 10 kD) against $ddH_2O$ for 24 hours (with multiple water changes) to remove any unbound $Fe^{3+}$. After dialysis, the iron bound to hNG-DFO that was present in the solution was directly measured using a GBC 932AA instrument. Based on DFO binding to $Fe^{3+}$ at a 1:1 molar ratio, the concentration of DFO was calculated.

The DFO conjugation levels for specific hNGs determined by above two methods were confirmed to be comparable.

Effect of emulsion size on nanogel properties was investigated. Varying the ratio of detergents can impact size of resulting nanogel formed. For example, a weight ratio of AOT to Brij 30 of 2:1 resulted in emulsions of approximately 214 nm in diameter with PDI 0.24, whereas a weight ratio of AOT to Brij 30 of 1:2 resulted in emulsions of 42 nm with PDI 0.20. In addition to template size, nanogel chemical composition was investigated by varying molar ratios of AAm, hGMA, and PEG-DA from 100:50:1 to 100:50:25 to 100:50:50, respectively.

Several other DFO-hNGs were prepared and characterized with the similar procedures described above. The results are summarized in Table 3.

TABLE 3 hNG-DFO composition and characterization.

| hNG-DFO | Molar ratio of AAm:hGMA:PEG-DA | z-average diameter (nm) | PDI | zeta-potential (mV) | DFO % (w/w) |
|---|---|---|---|---|---|
| hNG1-DFO* | 100:50:1 | 133.3 ± 1.9 | 0.25 ± 0.04 | −3.3 ± 0.1 | 30.7% |
| hNG2-DFO* | 100:50:25 | 34.1 ± 0.6 | 0.16 ± 0.02 | −4.3 ± 0.3 | 20.3% |
| hNG3-DFO* | 100:50:50 | 48.0 ± 0.9 | 0.14 ± 0.02 | 0.1 ± 0.1 | 18.2% |
| hNG4-DFO** | 100:50:1 | 107.0 ± 2.1 | 0.25 ± 0.04 | −11.2 ± 0.4 | 29.3% |
| hNG5-DFO** | 100:50:25 | 102.2 ± 0.7 | 0.18 ± 0.01 | −8.8 ± 0.3 | 19.7% |
| hNG6-DFO** | 100:50:50 | 307.7 ± 8.7 | 0.25 ± 0.01 | −5.0 ± 0.4 | 10.0% |

*The weight ratio of hexane:AOT:Brij 30:aqueous is 80:5:10:5 during reverse emulsion polymerization.
**The weight ratio of hexane:AOT:Brij 30:aqueous is 80:10:5:5 during reverse emulsion polymerization.

Figure 8:
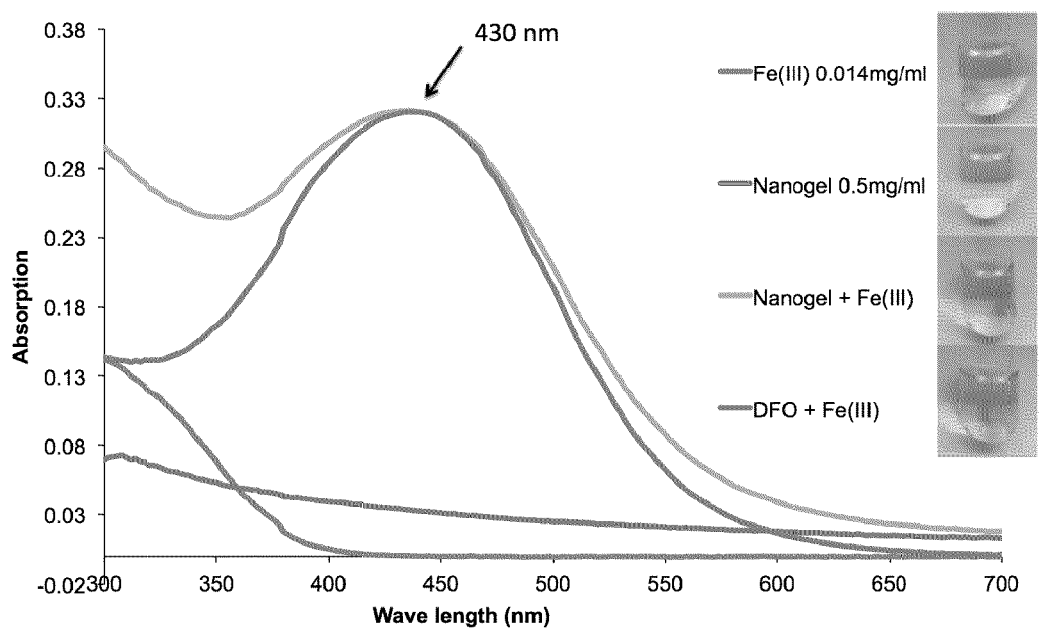
FIG. 8 shows UV-VIS absorption spectra of DFO and hNG-DFOs incubated with excess Fe(III).

FIG. 8 shows the UV-Vis absorption spectra of DFO and hNG2-DFO incubated with excess Fe(III). The spectra of DFO:Fe(III) and hNG2-DFO:Fe(III) reveal a maximum absorption at 430 nm, indicative of iron chelation (solutions have a yellow color) to free DFO or to hNG2-DFO (solutions are colorless).

Example 4: Chelation of Iron by hNG-DFO when Co-Incubated with Ferritin

Figure 9:
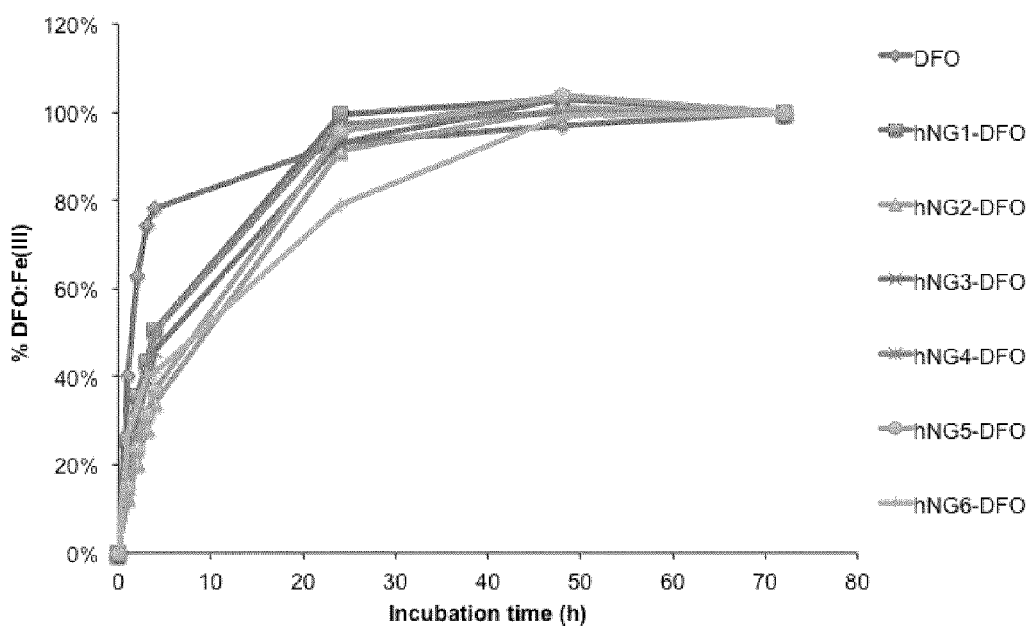
FIG. 9 shows plots of the percentage of iron chelation by hNG-DFOs over 72 hours.

For this assay, 1 mg/mL ferritin and 1 mg/mL the nanogel prepared in Example 1 were dissolved in pH 7.4 phosphate buffer and co-incubated at 37° C. The color of the mixture slowly changed from light yellow to a darker orange, indicating that more and more $Fe^{3+}$ was indeed being chelated to hNG-DFO as a function of time. Again, absorption at 430 nm was measured at different time points up to 72 h. The result was plotted as the % iron chelated to hNG-DFO, or hNG-DFO:Fe(III), in the presence of ferritin with respect to time:

hNG-DFO:Fe(III)=100×($A_{meas}$/$A_{max}$)%

Where $A_{meas}$ is the absorbance of hNG-DFO incubated with ferritin over time and $A_{max}$ is the maximum absorption of hNG-DFO incubated with excess free $Fe^{3+}$. FIG. 9 shows the plots of the percentage of iron chelation level for various hNGs over 72 hours.

Example 5: hNG-DFO Degradation in 1 M NaOH Solution

A 2 mg/mL solution of hNG-DFO (prepared as in Example 1) in 1M NaOH was incubated at room temperature for up to 5 days and Gel Permeation Chromatography (GPC) was used to monitor the degradation of hNG-DFO over time.

Figure 10:
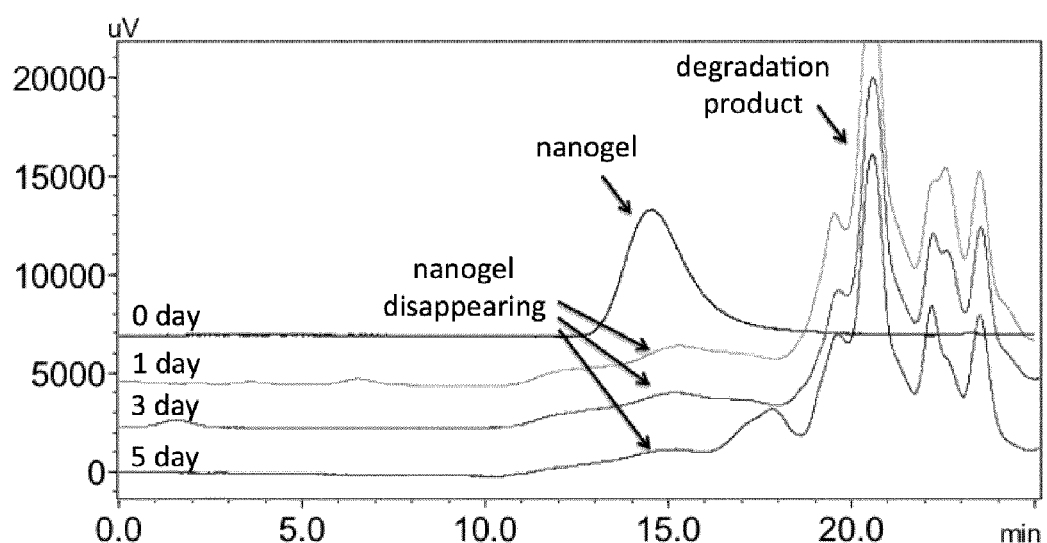
FIG. 10 shows GPC chromatograms of a hNG-DFO incubated in 1M NaOH solution.

FIG. 10 shows a GPC chromatogram of hNG2-DFO incubated in 1M NaOH at RT over 5-days. Due to the nature of gel permeation chromatography, larger particles elute earlier than smaller particles and molecules. The peak of nanogel at 14.3 minutes disappeared over the 5-day period, while peaks of smaller degradation products showed up between 16.0 and 25.0 minutes. Under these harsh conditions, most of the hNG-DFO particles were degraded by day 1.

Example 6: Cytotoxicity of hNG-DFO Particles

Human umbilical vein endothelial cells (HUVEC) were obtained from Lonza, Inc., and cultured at 37° C./5% $CO_2$ in EGM-2 complete medium. For the cytotoxicity assay, cells were seeded into 96-well plates at a density of 3,000 cell/well and allowed to equilibrate for 2 days before treatment. Free DFO and hNG-DFO stock solutions were made up to a final equivalent concentration of 1 mM DFO in the media, and cells were treated with serial dilution of DFO or hNG-DFO for 48 h before the cell viability was measured with the metabolism-based resazurin assay. The substrate resazurin was dissolved in cell culture medium at a concentration of 44 µM, added to each well and incubated at 37° C./5% $CO_2$ for 2.5 hours. The fluorescence of each well was measured using a SpectraMax Gemini EM microplate reader, with excitation at 560 nm and emission at 590 nm. Readings from the wells without cells were used as blanks ($E_{blank}$), and the readings taken from control cells without treatment ($E_{control}$) 1 represented 100% cell viability. The viability of treated cells at each concentration can be calculated by the following equation:

$$\text{Cell Viability} = 100 \times (E_{sample} - E_{blank})/(E_{control} - E_{blank})\%$$

FIGS. 11A and 11B show cytotoxicity profiles for HUVEC cells incubated with free DFO and hNG-DFOs after 48 h. From the interception of dose response curves and 50% cell viability line, it is clearly demonstrated that in order to inhibit 50% cell growth, it would require ~2 µM DFO but more than 100 µM hNG-DFO, meaning that hNG-DFO are much less toxic than DFO.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms or subunits refers to groups having 1, 2, or 3 atoms or subunits. Similarly, a group having 1-5 atoms or subunits refers to groups having 1, 2, 3, 4, or 5 atoms or subunits, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A composition comprising at least one cross-linked polyacrylyl co-polymer, wherein:

the cross-linked polyacrylyl co-polymer comprises water soluble acrylyl subunits, stimuli-responsive cross-linking subunits, and iron-chelating subunits, wherein each subunit is attached to at least one or two other subunits at the former vinyl carbons;

wherein the composition is a nanogel, and the water soluble acrylyl subunits are derived from acrylamido and/or acrylic monomers selected from the group consisting of acrylamide, methacrylamide, acrylic acid, and methacrylic acid monomers;

the stimuli-responsive cross-linking subunits are derived from hydrolyzable diacrylyl monomers or redox-sensitive diacrylyl complexes selected from the group consisting of hydrolyzable diacrylate monomers, redox-sensitive diacrylamide monomer complexes, hydrolyzable acrylate-acrylamide monomers, hydrolyzable vinyl-acrylate monomers, redox-sensitive vinyl-acrylamide monomer complexes, and redox-sensitive divinyl monomer complexes; and the iron-chelating subunits are derived from acrylyl or vinyl monomers comprising an iron chelating group;

wherein the iron chelating subunits are represented by Formula I or II

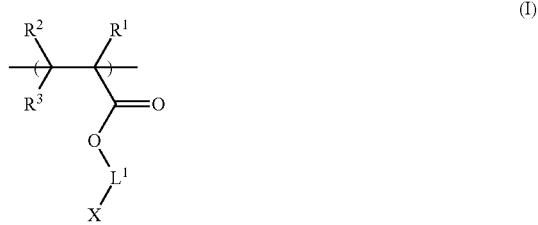

(II)

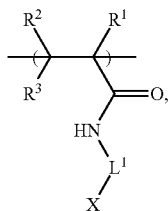

wherein:
R¹ at each occurrence is independently H, CN, or a $C_{1-4}$ alkyl group;
R² and R³ at each occurrence are independently H or methyl;
L¹ at each occurrence is independently a substituted or unsubstituted $C_{1-12}$ alkylene, substituted or unsubstituted $C_{1-12}$ heteroalkylene, or —$(CH_2CH_2O)_n$—, wherein n is 1, 2, 3, or 4; and
X is an iron chelating group.

2. The composition of claim 1 wherein the cross-linked polyacrylyl co-polymer further comprises one or more subunits derived from monomers selected from the group consisting of 2-hydroxyethyl methacrylate, N,N-diethylaminoethyl methacrylate, pegylated acrylamide, pegylated methacrylamide, pegylated acrylate, and pegylated methacrylate.

3. The composition of claim 1, wherein X is a group selected from deferoxamine, deferiprone, ethylenediaminetetraacetic acid, pyridoxal isonicotinoyl hydrazone, rhodotorulic acid, N,N'-Bis(2-hydroxybenzyl)ethylenediamine-N,N'-diacetic acid, N,N'-Bis(2-hydroxybenzyl)propylene-1,3-diamine-N,N'-diacetic acid, pyridoxal isonicotinoyl hydrozone, or 2,3-dihydroxybenzoic acid.

4. The composition of claim 1, wherein the iron chelating subunit is represented by Formula I, R¹ is a methyl, L¹ is ethylene, and X is deferoxamine.

5. The composition of claim 1, wherein the stimuli responsive cross-linking subunits are hydrolyzable diacylate monomers derived from poly(ethylene glycol) diacrylate monomers of Formula III-A,

III-A

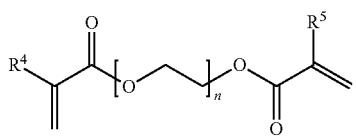

wherein:
R⁴ and R⁵ are independently H, CN, or a $C_{1-4}$ alkyl group; and
n is 1 to 20.

6. The composition of claim 1 wherein the cross-linked polyacrylyl co-polymer further comprises one or more subunits derived from monomers of Formula III-B or III-C:

III-B

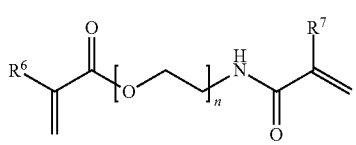

III-C

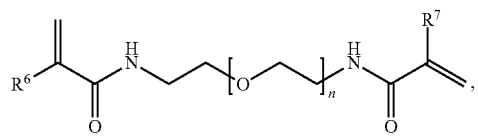

wherein:
R⁶ and R⁷ are independently H, CN, or a $C_{1-4}$ alkyl group; and
n is 1 to 20.

7. The composition of claim 1, wherein the cross-linking subunits are derived from redox sensitive diacrylyl monomer complexes.

8. The composition of claim 7, wherein the cross-linking subunits comprise ferrocenyl-containing subunits and ferrocenyl-binding subunits.

9. The composition of claim 8, wherein the ferrocenyl-binding subunits are selected from the structures of Formula V-B or V-D, (V-B)

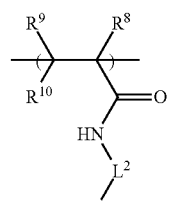

(V-D)

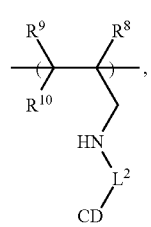

(V-D)

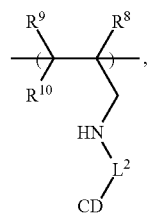

wherein:
CD at each occurrence is independently a ferrocenyl-binding cyclodextrin,
R⁸ at each occurrence is independently H, CN, or a $C_{1-4}$ alkyl group;
R⁹ and R¹⁰ at each occurrence are independently H or methyl; and
L² at each occurrence is independently a substituted or unsubstituted $C_{1-12}$ alkylene, substituted or unsubstituted $C_{1-12}$ heteroalkylene, or —$(CH_2CH_2O)_n$—, wherein n is 1, 2, 3, or 4.

10. The composition of claim 8, wherein the ferrocenyl-containing subunits have a structure selected from one or more of Formulae VII-A, VII-C, or VII-E:

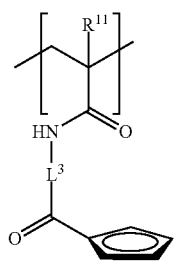

(VII-A)

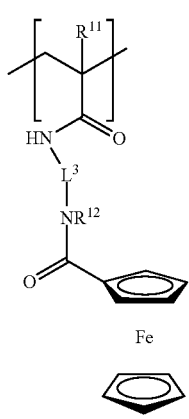

(VII-C)

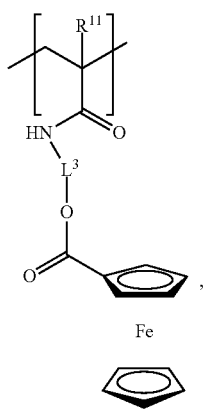

(VII-E)

wherein:
$R^{11}$ and $R^{12}$ at each occurrence are independently selected from H, CN, or a $C_{1-4}$ alkyl group; and
$L^3$ at each occurrence is independently a substituted or unsubstituted $C_{1-6}$ alkylene, or $C_{1-6}$ heteroalkylene group.

11. The composition of claim 8, wherein the redox-sensitive cross-linking subunits are derived from redox-sensitive monomer complexes having the following structure:

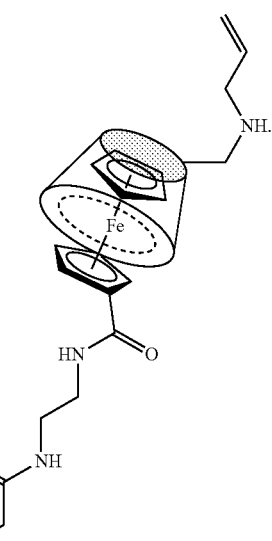

12. The composition of any one of claim 1, wherein the nanogel has a size of from about 10 to about 500 nm.

13. A method of treatment comprising administering to a subject at risk for or suffering from excess iron an effective amount of the composition of claim 1.

14. The method of claim 13, wherein the subject is a human.

15. The method of claim 13, wherein the subject suffers from excess iron due to a transfusion of red blood cells.

16. A process of making a composition of claim 1 comprising polymerizing a mixture of water soluble monomers, cross-linking monomers, and iron chelating monomers.

17. A composition comprising at least one cross-linked polyacrylyl co-polymer, wherein:
the cross-linked polyacrylyl co-polymer comprises water soluble acrylyl subunits, stimuli-responsive cross-linking subunits, and iron-chelating subunits wherein each subunit is attached to at least one or two other subunits at the former vinyl carbons;

wherein the composition is a nanogel, and wherein:
the water soluble acrylyl subunits are derived from acrylamido and/or acrylic monomers selected from the group consisting of acrylamide, methacrylamide, acrylic acid, and methacrylic acid monomers;

the stimuli-responsive cross-linking subunits are derived from the group consisting of redox-sensitive diacrylamide monomer complexes, redox-sensitive vinyl-acrylamide monomer complexes, and redox-sensitive divinyl monomer complexes; and the iron-chelating subunits are derived from acrylyl or vinyl monomers comprising an iron chelating group;
wherein the iron chelating subunits are represented by Formula I

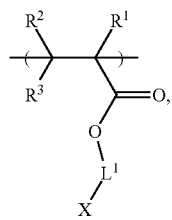

wherein:
R¹ is methyl;
R² and R³ at each occurrence are independently H or methyl;
L¹ is ethylene; and
X is an iron chelating group consisting of deferoxamine.

18. The composition of claim 17, wherein the water-soluble subunit is derived from acrylamide or methacrylamide.

19. The composition of claim 17, wherein the redox-sensitive monomer complexes comprise ferrocenyl-containing subunits and ferrocenyl-binding subunits having the following structure:

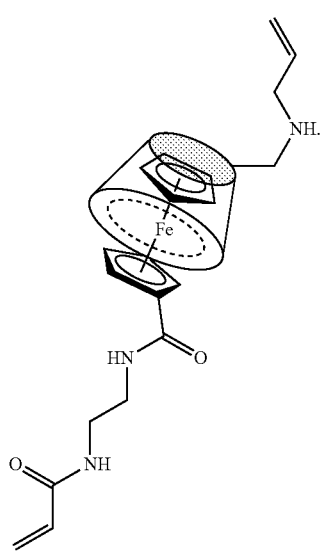

* * * * *